United States Patent
Bergens et al.

(10) Patent No.: US 9,592,497 B2
(45) Date of Patent: Mar. 14, 2017

(54) PROCESS FOR THE ASYMMETRIC HYDROGENATION OF IMIDES

(75) Inventors: Steven H. Bergens, Edmonton (CA); Satoshi Takebayashi, Tokyo (JP)

(73) Assignee: THE GOVERNORS OF THE UNIVERSITY OF ALBERTA, Edmonton (CA)

(*) Notice: Subject to any disclaimer, the term of this patent is extended or adjusted under 35 U.S.C. 154(b) by 19 days.

(21) Appl. No.: 13/378,923

(22) PCT Filed: Jun. 17, 2010

(86) PCT No.: PCT/CA2010/000926
§ 371 (c)(1),
(2), (4) Date: Mar. 9, 2012

(87) PCT Pub. No.: WO2010/145024
PCT Pub. Date: Dec. 23, 2010

(65) Prior Publication Data
US 2012/0165546 A1 Jun. 28, 2012

Related U.S. Application Data

(60) Provisional application No. 61/218,615, filed on Jun. 19, 2009.

(51) Int. Cl.
| | | |
|---|---|---|
| C07C 231/12 | (2006.01) |
| B01J 31/00 | (2006.01) |
| C07B 31/00 | (2006.01) |
| C07B 53/00 | (2006.01) |
| B01J 31/24 | (2006.01) |
| B01J 31/12 | (2006.01) |
| B01J 31/18 | (2006.01) |

(52) U.S. Cl.
CPC ......... *B01J 31/2409* (2013.01); *B01J 31/121* (2013.01); *B01J 31/1805* (2013.01); *C07B 53/00* (2013.01); *B01J 2231/643* (2013.01); *B01J 2531/0266* (2013.01); *B01J 2531/821* (2013.01)

(58) Field of Classification Search
CPC .................................................. B01J 31/2243
See application file for complete search history.

(56) References Cited

FOREIGN PATENT DOCUMENTS

WO    WO-2004-039777 A1    5/2004

OTHER PUBLICATIONS

Aoun et al., "Concomitant monoreduction and hydrogenation of unsaturated cyclic imides to lactams catalyzed by ruthenium compounds," *Angew. Chem. Int. Ed. Engl.* 44: 2021-2023, 2005.
Extended European Search Report in European Application No. 10788565.9 dated Feb. 1, 2013.
Hamilton and Bergens, "Direct observations of the metal-ligand bifunctional addition step in an enantioselective ketone hydrogenation," *J. Am. Chem. Soc.* 130: 11979-11987, 2008.
Ito et al., "Chemoselective hydrogenation of imides catalyzed by Cp*Ru(PN) complexes and its application to the asymmetric synthesis of paroxetine," *J. Am. Chem. Soc.* 129: 290-291, 2007.
Ito, "Hydrogenation of polar functionalities with Cp*Ru(PN) catalysts," *Pure Appl. Chem.* 80: 1047-1053, 2008.
Takebayashi et al., "Desymmetrization of meso-cyclic imides via enantioselective monohydrogenation," *J. Am. Chem. Soc.* 132: 12832-12834, 2010.
Mukaiyama, et al. "An asymmetric synthesis of bicyclic lactones and its application to the asymmetric synthesis of (1R,3S)-CIS-chrysanthemic acid," Chem Lett. 385-388 (1983).
Atodiresei et al., "Stereoselective anhydride openings," Chem Rev. 107:5683-5712 (2007).
Miller et al., "Enantiomerically pure polyhydroxylated acyliminium ions. Synthesis of the glycosidase inhibitors (−)-swainsonine and (+)-castanospermine," J Am Chem Soc. 112(22):8100-8112 (1990).
Chen et al., "Synthetic studies on d-Biotin, Part 9. An improved asymmetric synthetic route to d-Biotin via Hoffman-Roche lactone-thiolactone approach," Chem Pharm Bull. 53(7):743-746 (2005).
Royer et al., "Chiral heterocycles by iminium ion cyclization," Chem Rev. 104(5):2311-2352 (2004).
Maryanoff et al., "Cyclizations of N-acyliminium ions," Chem Rev. 104:1431-1628 (2004).
Speckamp et al., "New developments in the chemistry of N-acyliminium ions and related intermediates," Tetrahedron. 56:3817-3856 (2000).
Yazici et al., "Intermolecular addition reactions of N-acyliminium ions (Part I)," Synthesis. 3:339-368 (2009).
Yazici et al., "Intermolecular addition reactions of N-acyliminium ions (Part II)," Synthesis. 4:513-541 (2009).
Hamilton et al., "A ruthenium-dihydrogen putative intermediate in ketone hydrogenation," J Am Chem Soc. 127(12):4152-4153 (2005).
Hamilton et al., "An unexpected possible role of base in asymmetric catalytic hydrogenations of ketones. Synthesis and characterization of several key catalytic intermediates," J Am Chem Soc. 128(42):13700-13701 (2006).
Takebayashi et al., "Facile bifunctional addition of lactones and esters at low temperatures. The first intermediates in lactone/ester hydrogenations," Organometallics. 28(8):2349-2351 (2009).
Ito et al., "Hydrogenation of N-acylcarbamates and N-acylsulfonamides catalyzed by a bifunctional [Cp*Ru(PN)] complex," Angew Chem Int Ed. 48:1324-1327 (2009).
Written Opinion for International Patent Application No. PCT/CA2010/000926, dated Sep. 29, 2010 (5 pages).
International Search Report for International Patent Application No. PCT/CA2010/000926, mailed Oct. 25, 2010 (2 pages).
International Preliminary Report on Patenability for International Patent Application No. PCT/CA2010/000926, dated Oct. 21, 2011 (5 pages).
Communication pursuant to Article 94(3) EPC for European Patent Application No. 10788565.9, dated Jul. 5, 2016 (5 pages).

*Primary Examiner* — Nyeemah A Grazier
(74) *Attorney, Agent, or Firm* — Clark & Elbing LLP

(57) ABSTRACT

The present disclosure provides a process for the mono-reduction of one or more imide moieties in a compound comprising contacting the compound with hydrogen gas and a catalyst comprising a transition metal hydride in the presence of a base, under conditions for the mono-reduction of the one or more imide moieties to form a compound comprising one or more hydroxy amides.

22 Claims, 1 Drawing Sheet

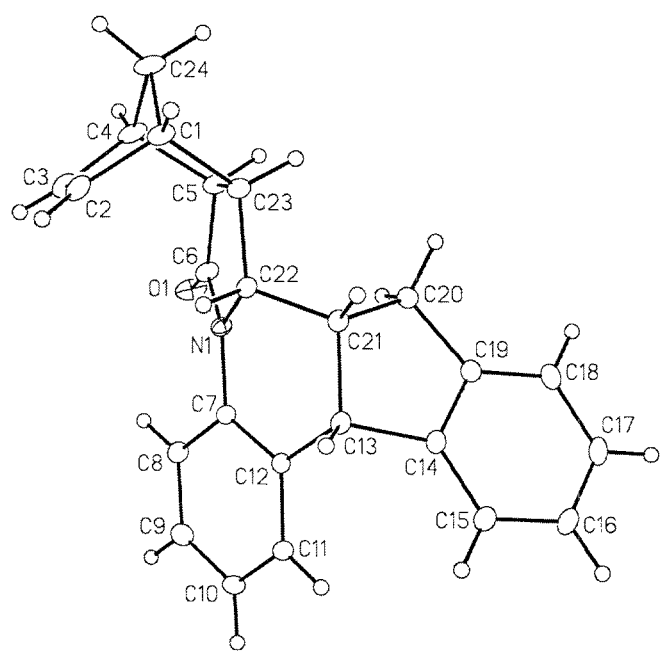

PROCESS FOR THE ASYMMETRIC HYDROGENATION OF IMIDES

CROSS-REFERENCE TO RELATED APPLICATIONS

This application is the United States national stage filing under 35 U.S.C. §371 of International patent application PCT/CA2010/000926 filed Jun. 17, 2010, which claims priority from U.S. patent application 61/218,615, filed Jun. 19, 2009. Both of these applications are hereby incorporated by reference in their entirety.

FIELD OF THE DISCLOSURE

The present disclosure relates to the field of catalytic hydrogenation, in particular the catalytic asymmetric monohydrogenation of imides.

BACKGROUND OF THE DISCLOSURE

In contrast with the innumerable reports of enantioselective olefin and ketone hydrogenations in the literature, there are very few reports of homogenous hydrogenations of imides (Bruneau et al, Angew. Chem. Int. 2005, 44, 2021; Ikariya et al J. Am. Chem. Soc 2007, 129, 290; Ikariya et al, Angew. Chem. Int. 2009, 48, 1324). These literature hydrogenations of imides require extreme conditions (~80° C., 30-60 atm $H_2$) and also result in ring-opening of the imide by direduction (Scheme 1).

Scheme 1

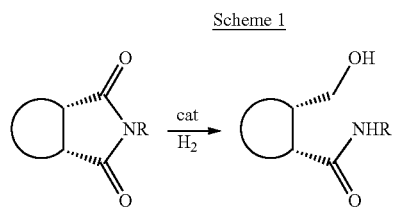

There appear to be no reports in the literature of the mono-reduction of an imide to the hydroxy lactam by homogeneous hydrogenation, notwithstanding an enantioselective version of this reaction. However, there are reports of enantioselective imide reductions using main-group hydride reducing agents that illustrate the potential of this hydrogenation (Asami et al. Chem. Lett. 1983, 385). In particular, LAH-type reagents have been utilized to carry out the desymmetrization of the cyclopropane-derived imide 1 in 83% ee. The hydroxy lactam was subsequently converted into (1R,3S)-cis-chrysanthemic acid (Scheme 2).

Scheme 2

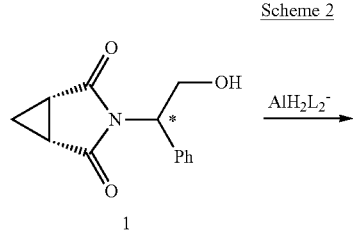

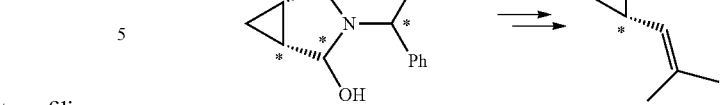

The desymmetrization of the imide 2 with various chiral LAH reagents in effort to prepare (~)-Swainsonine (Scheme 3) has also been investigated (Chamberlin et al. J. Amer. Chem. Soc., 1990, 112, 8100).

Scheme 3

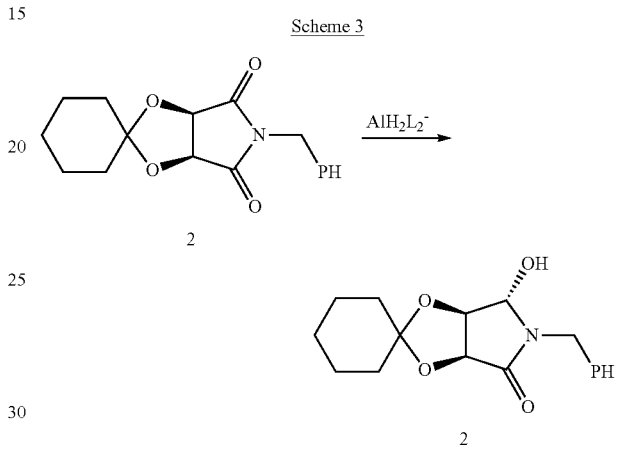

As a final illustration, the desymmetrization of 3 with a reusable, polymer-bound chiral B—H reagent in 98% ee was also examined (Chen et al., Chem Pharm Bull 2005, 53, 743). The hydroxy lactam was subsequently converted into (+)-Biotin (Scheme 4).

Scheme 4

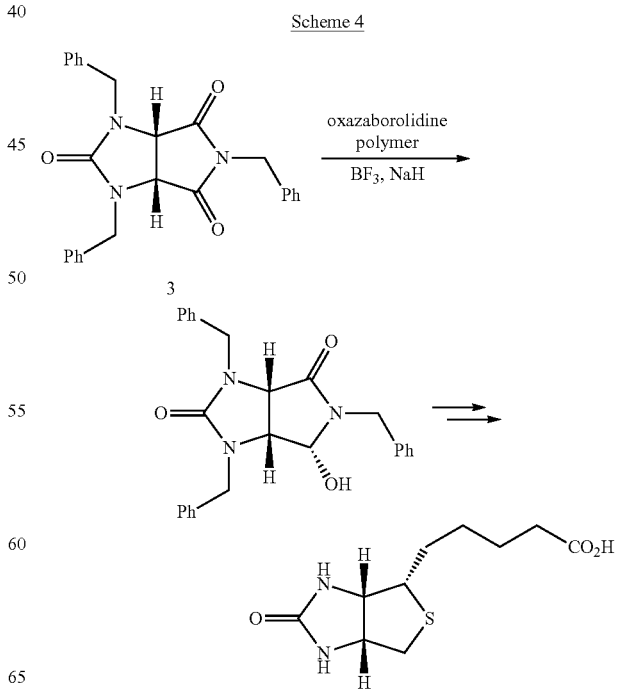

Desymmetrization reactions that produce multiple stereogenic centers in a single enantioselective event are highly sought after in the academic and industrial synthetic communities. An extensive review of the desymmetrization of meso anhydrides and its use in the preparation of several classes of compounds was recently reported (Bolm, et al. Chem. Rev. 2007, 107:5683-5712).

Hydroxy lactams are useful building blocks for a variety of biologically significant molecules. They are particularly useful as precursors to iminium ions (Royer et al., Chem. Rev., 2004, 104, 2311-2352; Maryanoff et al., Chem. Rev. 2004, 104, 1431-1628; Speckamp et al., Tetrahedron, 2000, 56, 3817-3856; Pyne et al., Synthesis, 2009, 3, 339-368; Pyne et al., 2009, 4, 513-541).

SUMMARY OF THE DISCLOSURE

It has now been determined that transition metal hydride catalysts in the presence of hydrogen gas and a base are effective for the catalytic mono-reduction of compounds containing an imide moiety.

Accordingly, the present disclosure provides a process for the mono-reduction of one or more imide moieties in a compound comprising contacting the compound with hydrogen gas and a catalyst comprising a transition metal hydride in the presence or absence of a base, under conditions for the mono-reduction of the one or more imide moieties to form a compound comprising one or more hydroxy amides.

In another embodiment of the disclosure, the transition metal hydride is a complex comprising a suitable transition metal M, and coordinated thereto, one to four ligands selected from:
  (i) a bidentate diphosphine (P—P) ligand,
  (ii) a bidentate diamino (N—N) ligand,
  (iii) a bidentate aminophosphine (P—N) ligand,
  (iv) a tridentate diaminophosphine (P—N—N) ligand,
  (v) a tridentate aminodiphosphine (P—N—P) ligand,
  (vi) a tetradentate diaminodiphosphine (P—N—N—P) ligand,
  (vii) a monodentate phoshine (P) ligand, and
  (viii) a monodentate amine (N) ligand;
one to three hydride ligands;
zero to two neutral monodentate ligands; and
zero to two anionic monodentate ligands, the complex being neutral or cationic, and if the complex is cationic, the complex further comprises one or more suitable counteranions.

In another embodiment of the disclosure, the transition metal, M, is Fe, Ru, Rh, Ir, Pd, Cu, Co, Pt, Ti, Zr or Hf. In another embodiment, the transition metal, M, is Ru, Fe or Rh. In another embodiment, the transition metal is Ru or Fe. In another embodiment, the transition metal is Ru.

In another embodiment, the bidentate diphosphine ligand (P—P) is a compound of the Formula (I):

$$R^1R^2P\text{-}Q^1\text{-}PR^3R^4 \qquad (I)$$

wherein
$R^1$, $R^2$, $R^3$ and $R^4$ are independently selected from $(C_{1-20})$-alkyl, $(C_{3-20})$-cycloalkyl and $(C_{6-18})$-aryl, each group being optionally substituted with one or more substituents independently selected from $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl, or
$R^1$ and $R^2$ and/or $R^3$ and $R^4$ are joined to form, together with the phosphorous atom to which they are attached, a saturated or unsaturated, monocyclic or polycyclic, substituted or unsubstituted ring system containing from 3 to 14 atoms, $Q^1$ is selected from unsubstituted or substituted $(C_{1-10})$-alkylene and unsubstituted or substituted $(C_{1-10})$-alkenylene where the substituents on $Q^1$ are independently selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and unsubstituted or substituted $(C_{6-14})$-aryl, and/or
adjacent substituents on $Q^1$ are joined together to form, including the carbon atoms to which they are attached, one or more unsubstituted or substituted 5-20-membered monocyclic, polycyclic, heterocyclic, carbocyclic, saturated, unsaturated or metallocenyl ring systems,
where the term substituted with respect to the $Q^1$ substituents means that one or more of the available hydrogen atoms on the group are replaced with $(C_{1-6})$-alkyl, fluoro-substituted $(C_{1-6})$-alkyl, $(C_{1-6})$-alkoxy, fluoro-substituted $(C_{1-6})$-alkoxy, halo or $(C_{6-14})$-aryl, and
$Q^1$ is chiral or achiral.

In a further embodiment, the compound of the Formula (I) is

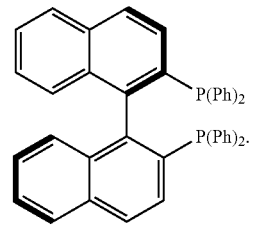

In another embodiment of the present disclosure, the bidentate diamino (N—N) ligand is a compound of the Formula (II):

$$R^5R^6N\text{-}Q^2\text{-}NR^7R^8 \qquad (II)$$

wherein
$R^5$, $R^6$, $R^7$ and $R^8$ are independently selected from H, $(C_{3-20})$-cycloalkyl and $(C_{6-18})$-aryl, the latter three groups each being optionally substituted with one or more substituents independently selected from $(C_{1-6})$-alkyl, fluoro-substituted $(C_{1-6})$-alkyl halo, $(C_{1-6})$-alkoxy, fluoro-substituted $(C_{1-6})$-alkoxy and $(C_{6-14})$-aryl, or
$R^5$ and $R^6$ and/or $R^7$ and $R^8$ are joined to form, together with the nitrogen atom to which they are attached, a saturated or unsaturated, monocyclic or polycyclic, substituted or unsubstituted ring system containing from 3 to 14 atoms, or
one of $R^5$ and $R^6$, and/or one of $R^7$ and $R^8$ are joined with a substituent on $Q^2$ to form, together with the nitrogen atom to which $R^5$, $R^6$, $R^7$ or $R^8$ is attached, a 4- to 10-membered saturated or unsaturated, monocyclic or bicyclic ring system, where if the nitrogen atom is bonded to an adjacent atom via a double bond, the other of $R^5$ or $R^6$ and $R^7$ or $R^8$ is not present,
$Q^2$ is selected from unsubstituted or substituted $(C_{1-10})$-alkenylene and unsubstituted or substituted $(C_{1-10})$-alkenylene where the substituents on $Q^2$ are independently selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and unsubstituted or substituted aryl, and/or
adjacent substituents on $Q^2$ are joined together to form, including the carbon atoms to which they are attached, one or more unsubstituted or substituted 5-20-membered monocyclic, polycyclic, heterocyclic, carbocyclic, saturated, unsaturated or metallocenyl ring systems,
where the term substituted with respect to the $Q^2$ substituents means that one or more of the available hydrogen atoms on the group are replaced with $(C_{1-6})$-alkyl, fluoro-substituted $(C_{1-6})$-alkyl, $(C_{1-6})$-alkoxy, fluoro-substituted $(C_{1-6})$-alkoxy, halo or $(C_{6-14})$-aryl, and
$Q^2$ is chiral or achiral.

In another embodiment, the compound of the Formula (II) is

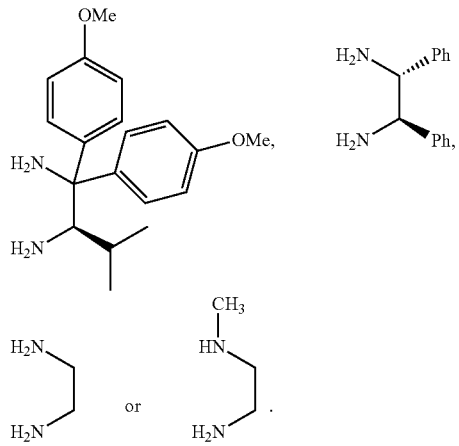

In another embodiment, the compound of the Formula (II) is

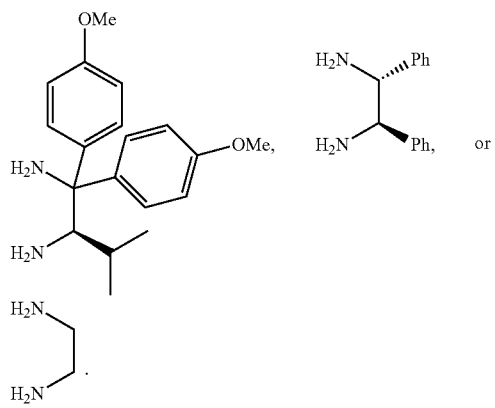

In a further embodiment of the disclosure, the bidentate aminophosphine (P—N) ligand is a compound of the Formula (III)

$$R^9R^{10}P\text{-}Q^3\text{-}NR^{11}R^{12} \tag{III}$$

wherein $R^9$ and $R^{19}$ are independently as defined for $R^1$-$R^4$ as defined in Formula (I), $R^{11}$ and $R^{12}$ are independently as defined for $R^5$-$R^8$ as defined in Formula (II), and $Q^3$ is as defined for $Q^1$ as defined in Formula (I).

In another embodiment, the tridentate diaminophosphine (P—N—N) ligand is a compound of the Formula (IV):

$$R^{13}R^{14}P\text{-}Q^4\text{-}NR^{15}\text{-}Q^5\text{-}NR^{16}R^{17} \tag{IV}$$

wherein
$R^{13}$ and $R^{14}$ are independently as defined for $R^1$ and $R^2$ as defined in Formula (I), $Q^4$ and $Q^5$ are as defined for $Q^1$ as defined in Formula (I), $R^{15}$ is selected from H, $(C_{1-20})$-alkyl, $(C_{3-20})$-cycloalkyl and $(C_{6-18})$-aryl, the latter three groups each being optionally substituted with one or more substituents independently selected from $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl, or $R^{15}$ is joined with a substituent on $Q^4$ and/or $Q^5$ to form, together with the nitrogen atom to which $R^{15}$ is attached, a 4- to 10-membered saturated or unsaturated, monocyclic or bicyclic ring system, $R^{16}$ and $R^{17}$ are independently as defined for $R^5$-$R^8$ as defined in Formula (II).

In another embodiment, the tridentate diaminophosphine (P—N—P) ligand is a compound of the Formula (V):

$$R^{18}R^{19}P\text{-}Q^6\text{-}NR^{20}\text{-}Q^7\text{-}PR^{21}R^{22} \tag{V}$$

wherein
$R^{18}$, $R^{19}$, $R^{21}$ and $R^{22}$ are independently as defined for $R^1$ and $R^2$ as defined in Formula (I), $Q^6$ and $Q^7$ are as defined for $Q^1$ as defined in Formula (I), $R^{20}$ is as defined as $R^{15}$ as defined in Formula (IV).

In another embodiment, the tetradentate diaminodiphosphine (P—N—N—P) ligand is a compound of the Formula (VIa) or (VIb):

$$R^{23}R^{24}P\text{-}Q^8\text{-}NR^{25}\text{-}Q^9\text{-}NR^{26}\text{-}Q^{10}\text{-}PR^{27}R^{28} \tag{VIa}$$

$$R^{23}R^{24}P\text{-}Q^8\text{=}N\text{-}Q^9\text{-}N\text{=}Q^{10}\text{-}PR^{27}R^{28} \tag{VIb}$$

wherein $R^{23}$, $R^{24}$, $R^{27}$ and $R^{28}$ are independently as defined for $R^1$ and $R^2$ in Formula (I);

$R^{25}$ and $R^{26}$ are independently as defined for $R^{15}$ in Formula (IV); and $Q^8$, $Q^9$ and $Q^{10}$ are independently as defined for $Q^1$ in Formula (I).

In another embodiment, the monodentate phosphine (P) ligand is a compound of the Formula (VII):

$$PR^{29}R^{30}R^{31} \tag{VII}$$

wherein $R^{29}$, $R^{30}$ and $R^{31}$ are independently as defined for $R^1$ and $R^2$ in Formula (I).

In a further embodiment, the monodentate amino (N) ligand is a compound of the formula (VIII):

$$NR^{32}R^{33}R^{34} \tag{VIII}$$

wherein $R^{32}$-$R^{34}$ are independently as defined for $R^5$-$R^8$ in Formula (II).

In another embodiment of the disclosure, the transition metal hydride is selected from

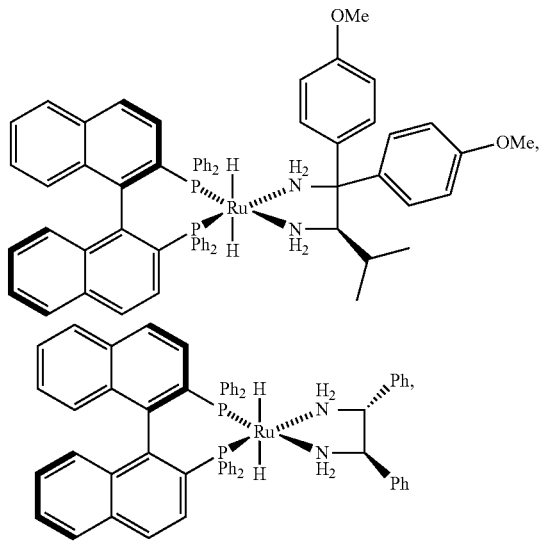

-continued

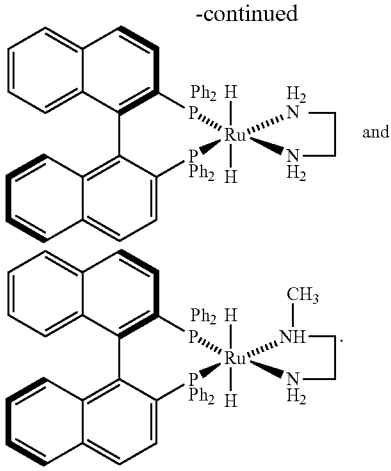

In another embodiment of the disclosure, the transition metal hydride is selected from

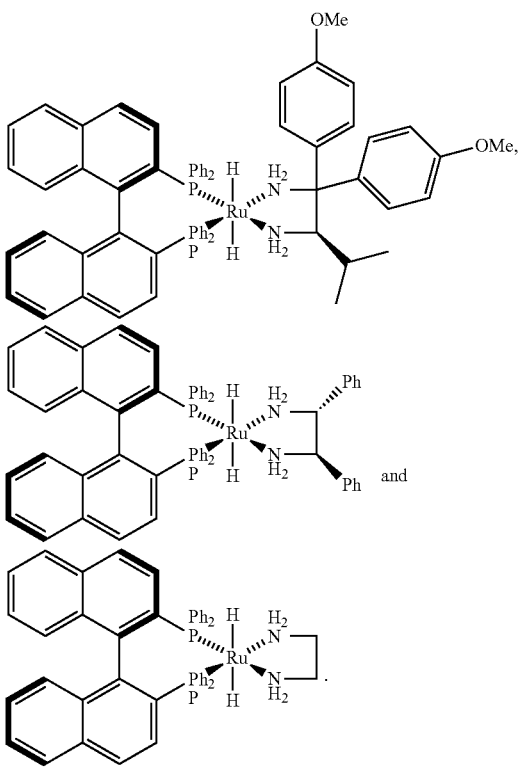

In an embodiment, the neutral monodentate ligand is any neutral two electron donor, such as water, acetonitrile, DMF, ammonia, pyridine, tetrahydrofuran (THF), CO, tBuCN or t-BuNC.

In another embodiment of the disclosure, the anionic monodentate ligand is any anionic two electron donor, such as halo (fluoro, chloro, bromo or iodo), $(C_{1-6})$-alkoxy, hydroxy, $BF_4^-$, $AlH_4^-$, thiocyanate, cyano, carboxylate, sulfonates and nitrates.

In another embodiment, the counteranion is any non-coordinating counter anion, such as OTf⁻, $BF_4^-$ and $PF_6^-$.

In a further embodiment of the disclosure, the compound comprising one or more imide moieties is a compound of the Formula (IX)

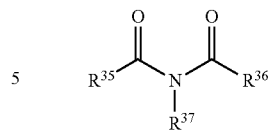

wherein
$R^{35}$ and $R^{36}$ are independently selected from $(C_{1-20})$-alkyl, $(C_{3-20})$-cycloalkyl and $(C_{6-18})$-aryl, each group being optionally substituted, wherein the optional substituents are independently selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl and/or one or more of the carbon atoms is optionally replaced with a heteromoiety selected from O, S, N, NH and N—$(C_{1-6})$-alkyl, or $R^{35}$ and $R^{36}$ are joined together to form, including the carbon atoms to which they are attached and the imide nitrogen, an unsubstituted or substituted 5-20-membered monocyclic, polycyclic, heterocyclic, carbocyclic, saturated or unsaturated ring system, wherein the optional substituents are selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl, and $R^{37}$ is selected from H, $(C_{1-6})$-alkyl, $(C_{3-8})$-cycloalkyl and $(C_{6-14})$-aryl, the latter three groups being optionally substituted with one or more of $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl and/or one or more of the carbon atoms is optionally replaced with a heteromoiety selected from O, S, N, NH and N—$(C_{1-6})$-alkyl; and where the compound of Formula (IX) is chiral or achiral.

In another embodiment, $R^{35}$ and $R^{36}$ are joined to form, including the carbon atoms to which they are attached and the imide nitrogen, a ring system selected from:

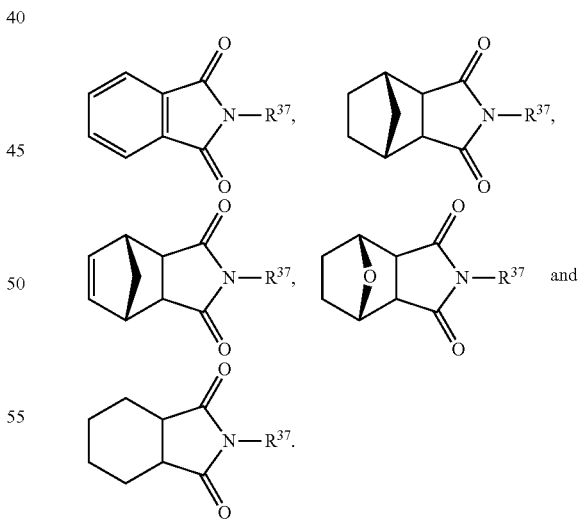

In another embodiment, the base is an organic non-coordinating base or a salt of a carbonate, a carboxylate, an alcoholate, a hydroxide or a silazide.

In a further embodiment, the process is performed in a suitable organic solvent.

In another embodiment of the disclosure, the hydrogen gas is used at a pressure in the range of about 1 atm to about 100 atm. In another embodiment, the hydrogen gas is used at a pressure of about 50 atm.

In another embodiment of the disclosure, the process is performed at a temperature of about −20° C. to about 60° C.

An advantage of the process of the present disclosure is that the transition metal hydride catalysts of the present disclosure, when contacted with the compound comprising one or more imide moieties of the Formula (IX), result in the mono-reduction of the imide moiety, to form a compound of the Formula (Xa) or (Xb):

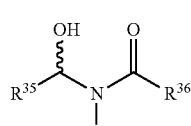

(Xa)

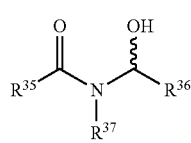

(Xb)

wherein $R^{35}$-$R^{37}$ are as defined for Formula (IX) and the compound of the Formulae (Xa) or (Xb) is chiral or achiral.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The present disclosure will now be described in greater detail with reference to the following drawings in which:

FIG. 1 shows an X-ray crystallographic structure of the reaction product of a hydroxy-lactam and indene in an embodiment of the disclosure.

DETAILED DESCRIPTION OF THE DISCLOSURE

Definitions

The term "$(C_{1-n})$-alkyl" as used herein means straight and/or branched chain, saturated alkyl radicals containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl radical.

The term "$(C_{2-n})$-alkenyl" as used herein means straight and/or branched chain, unsaturated alkyl radicals containing from two to n carbon atoms and one or more, suitably one to three, double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl radical.

The term "$(C_{2-n})$-alkynyl" as used herein means straight and/or branched chain, unsaturated alkyl groups containing from one to n carbon atoms and one or more, suitably one to three, triple bonds, and includes (depending on the identity of n) ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl-4-methylpent-2-ynyl, 1-hexynyl and the like, where the variable n is an integer representing the largest number of carbon atoms in the alkynyl radical.

The term "$(C_{3-n})$-cycloalkyl" as used herein means a monocyclic or polycyclic saturated carbocyclic group containing from three to n carbon atoms and includes (depending on the identity of n) cyclopropyl, cyclobutyl, cyclopentyl, cyclodecyl, bicyclo[2.2.2]octane, bicyclo[2.2.1]heptane, bicyclo[3.1.1]heptane and the like, where the variable n is an integer representing the largest number of carbon atoms in the cycloalkyl radical.

The term "$(C_{3-n})$-cycloalkenyl" as used herein means a monocyclic or polycyclic carbocyclic group containing from three to n carbon atoms (depending on the identity of n) and one or more, suitably one or two, double bonds and includes cyclopropenyl, cyclobutenyl, cyclopentenyl, cyclodecenyl, bicyclo[2.2.2]oct-2-ene, bicyclo[2.2.1]hept-2-ene, bicyclo[3.1.1]hept-2-ene and the like, where the variable n is an integer representing the largest number of carbon atoms in the cycloalkenyl radical.

The term "$(C_{3-n})$-cycloalkynyl" as used herein means a monocyclic or polycyclic carbocyclic group containing from three to n carbon atoms (depending on the identity of n) and one or more, suitably one or two, double bonds and includes cyclopropenyl, cyclobutynyl, cyclopentynyl, cyclohexynyl, cyclodecynyl, bicyclo[2.2.2]oct-2-yne, bicyclo[2.2.1]hept-2-yne, bicyclo[3.1.1]hept-2-yne and the like, where the variable n is an integer representing the largest number of carbon atoms in the cycloalkynyl radical.

The term "$(C_{6-n})$-aryl" as used herein means a monocyclic, bicyclic or tricyclic carbocyclic ring system containing from 6 to n carbon atoms and optionally a metal and includes, depending on the identity of n, phenyl, naphthyl, anthracenyl, 1,2-dihydronaphthyl, 1,2,3,4-tetrahydronaphthyl, fluorenyl, indanyl, indenyl, ferrocenyl, and the like, where the variable n is an integer representing the largest number of carbon atoms in the aryl radical.

The term "heteroaryl" as used herein means a monocyclic or polycyclic ring system containing one or two aromatic rings and from 5 to 14 atoms of which, unless otherwise specified, one, two, three, four or five are heteromoieties independently selected from N, NH, N—($C_{1-6}$)-alkyl, O and S and includes thienyl, furyl, pyrrolyl, pyrididyl, indolyl, quinolyl, isoquinolyl, tetrahydroquinolyl, benzofuryl, benzothienyl and the like.

The term "fluoro-substituted" with respect to any specified group as used herein means that the one or more, including all, of the hydrogen atoms in the group have been replaced with a fluorine, and includes trifluoromethyl, pentafluoroethyl, fluoromethyl and the like.

The suffix "ene" added on to any of the above groups means that the group is divalent, i.e. inserted between two other groups.

The term "ring system" as used herein refers to a carbon-containing ring system, that includes monocycles, fused bicyclic and polycyclic rings, bridged rings and metallocenes. Where specified, the carbons in the rings may be substituted or replaced with heteroatoms.

The term "unsaturated" with respect to ring systems includes aromatic and non-aromatic rings.

The term "suitable transition metal" as used herein refers to any transition metal that will form catalysts of the Formula (I) and are useful for the mono-reduction of imides. Transition metals that are useful for the mono-reduction of imides include, but are not limited to, Fe, Ru, Rh, Ir, Pd, Cu, Co, Pt, Ti, Zr and Hf.

The term "neutral monodentate ligand" as used herein refers to any neutral ligand which donates a single pair electrons and coordinates to the transition metal (M). Examples of neutral monodentate ligands include, but are not limited to, water, acetonitrile, DMF, ammonia, carbon monoxide, pyridine, tetrahydrofuran (THF), tBuCN or t-BuNC.

The term "anionic monodentate ligand" as used herein refers to any anionic ligand which donates a single pair electrons and coordinates to the transition metal (M). Examples of anionic monodentate ligands include, but are not limited to, halo (fluoro, chloro, bromo or iodo), $(C_{1-6})$-alkoxy, hydroxy, thiocyanate, cyano, carboxylate, sulfonates and nitrates.

The term "counteranion" as used herein refers to any counterion which is present when the transition metal hydride catalyst is cationic. Examples of counterions include, but are not limited to, OTf⁻, $BF_4^-$ and $PF_6^-$.

The term "transition metal hydride" as used herein refers to transition metal catalysts of the present disclosure in which the transition metal catalyst is coordinated to one, two, three or four hydrogen atoms. The active catalyst which is able to mono-reduce an imide moiety will have at least one hydride ligand. It will further be understood that more than four hydrogen atoms can be coordinated to the transition metal and still act as a catalyst for the processes of the present disclosure.

The terms "mono-reduction" or "mono-reduced" as used herein refers to the single reduction of one of the carbonyl functionalities in an imide moiety to the corresponding hydroxy group. An imide moiety has the Formula

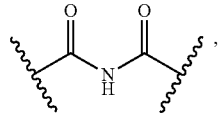 [SMILES: *C(=O)NC(*)=O]

and accordingly, the mono-reduction of the imide moiety results in the imide being reduced to

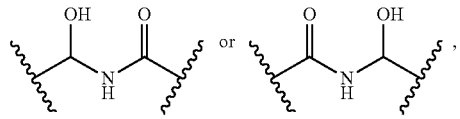 [SMILES: *C(=O)NC(*)O ; *C(=O)NC(*)O]

and depending on the nature of the imide moiety, the corresponding hydroxy compound may be chiral or achiral.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Process of the Disclosure

It has now been determined that transition metal hydride catalysts in the presence of hydrogen gas and a base are effective for the catalytic mono-reduction of compounds containing an imide moiety.

Accordingly, the present disclosure provides a process for the mono-reduction of one or more imide moieties in a compound comprising contacting the compound with hydrogen gas and a catalyst comprising a transition metal hydride in the presence or absence of a base, under conditions for the mono-reduction of the one or more imide moieties to form a compound comprising one or more hydroxy amides.

In another embodiment of the disclosure, the transition metal hydride is a complex comprising a suitable transition metal M, and coordinated thereto, one to four, optionally one to three, or one to two, or two, ligands selected from:
(i) a bidentate diphosphine (P—P) ligand,
(ii) a bidentate diamino (N—N) ligand,
(iii) a bidentate aminophosphine (P—N) ligand,
(iv) a tridentate diaminophosphine (P—N—N) ligand,
(v) a tridentate aminodiphosphine (P—N—P) ligand,
(vi) a tetradentate diaminodiphosphine (P—N—N—P) ligand,
(vii) a monodentate phoshine ligand (P), and
(viii) a monodentate amine (N) ligand;
one to three, optionally one to two, or two, or three, hydride ligands; zero to two, optionally zero, or one, or two, neutral monodentate ligands; and zero to two, optionally zero, or one, or two, anionic monodentate ligands, the complex being neutral or cationic, and if the complex is cationic, the complex further comprises one or more suitable counteranions.

In an embodiment, the active transition metal hydride catalyst comprises at least one or more, optionally one to three, or one to two, or two, hydride ligands.

In another embodiment of the disclosure, the transition metal, M, is Fe, Ru, Rh, Ir, Pd, Cu, Co, Pt, Ti, Zr and Hf. In another embodiment, the transition metal, M, is Ru, Fe or Rh. In another embodiment, the transition metal is Ru or Fe. In another embodiment, the transition metal is Ru.

In another embodiment, the bidentate diphosphine ligand (P—P) is a compound of the Formula (I):

$$R^1R^2P\text{-}Q^1\text{-}PR^3R^4 \qquad (I)$$

wherein
$R^1$, $R^2$, $R^3$ and $R^4$ are independently selected from $(C_{1-20})$-alkyl, $(C_{3-20})$-cycloalkyl and $(C_{6-18})$-aryl, each group being optionally substituted with one or more substituents independently selected from $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl, or
$R^1$ and $R^2$ and/or $R^3$ and $R^4$ are joined to form, together with the phosphorous atom to which they are attached, a saturated or unsaturated, monocyclic or polycyclic, substituted or unsubstituted ring system containing from 3 to 14 atoms,
$Q^1$ is selected from unsubstituted or substituted $(C_1\text{-}C_{10})$-alkylene and unsubstituted or substituted $(C_{1-10})$-alkenylene where the substituents on $Q^1$ are independently selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and unsubstituted or substituted $(C_{6-14})$-aryl; and/or adjacent substituents on $Q^1$ are joined together to form, including the carbon atoms to which they are attached, one or more unsubstituted or substituted 5-20-membered monocyclic, polycyclic, heterocyclic, carbocyclic, saturated, unsaturated or metallocenyl ring systems;
where the term substituted with respect to the $Q^1$ substituents means that one or more of the available hydrogen atoms on the group are replaced with $(C_{1-6})$-alkyl, fluoro-substituted $(C_{1-6})$-alkyl, $(C_{1-6})$-alkoxy, fluoro-substituted $(C_{1-6})$-alkoxy, halo or $(C_{6-14})$-aryl; and
$Q^1$ is chiral or achiral.

In another embodiment of the disclosure, $R^1$, $R^2$, $R^3$ and $R^4$ are independently selected from $(C_{1-6})$-alkyl, $(C_{3-10})$-cycloalkyl and phenyl, each group being optionally substituted with one to five, suitably one to three, substituents independently selected from $(C_{1-4})$-alkyl, fluoro-substituted $(C_{1-4})$-alkyl, halo, $(C_{1-4})$-alkoxy and fluoro-substituted $(C_{1-4})$-alkoxy;
$Q^1$ is selected from unsubstituted or substituted $(C_{1-6})$-alkylene where the substituents on $Q^1$ are independently selected from one to five, suitably one to three, of $(C_{1-4})$-alkyl, fluoro-substituted $(C_{1-4})$-alkyl, halo, $(C_{1-4})$-alkoxy, fluoro-substituted $(C_{1-4})$-alkoxy, unsubstituted and substituted phenyl and substituted and unsubstituted naphthyl, or adjacent substituents are joined together to form, including the carbon atoms to which they are attached, one or more unsubstituted or substituted phenylene, cyclohexylene, naphthylene, pyridylene or ferrocenylene groups; and $Q^1$ is chiral or achiral.

In another embodiment, $R^1$, $R^2$, $R^3$ and $R^4$ are all cyclohexyl, phenyl, xylyl or tolyl.

In a further embodiment, the compound of the Formula (I) is

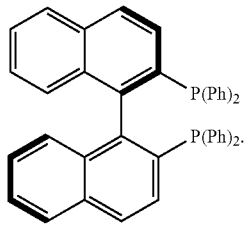

In another embodiment of the present disclosure, the bidentate diamino (N—N) ligand is a compound of the Formula (II):

$$R^5R^6N\text{-}Q^2\text{-}NR^7R^8 \qquad (II)$$

wherein
$R^5$, $R^6$, $R^7$ and $R^8$ are independently selected from H, $(C_{1-20})$-alkyl, $(C_{3-20})$-cycloalkyl and $(C_{6-18})$-aryl, the latter three groups each being optionally substituted with one or more substituents independently selected from $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl, or
$R^5$ and $R^6$ and/or $R^7$ and $R^8$ are joined to form, together with the nitrogen atom to which they are attached, a saturated or unsaturated, monocyclic or polycyclic, substituted or unsubstituted ring system containing from 3 to 14 atoms, or
one of $R^5$ and $R^6$, and/or one of $R^7$ and $R^8$ are joined with a substituent on $Q^2$ to form, together with the nitrogen atom to which $R^5$, $R^6$, $R^7$ or $R^8$ is attached, a 4- to 10-membered saturated or unsaturated, monocyclic or bicyclic ring system, where if the nitrogen atom is part of aromatic ring or is bonded to an adjacent atom via a double bond, the other of $R^5$ or $R^6$ and $R^7$ or $R^8$ is not present,
$Q^2$ is selected from unsubstituted or substituted $(C_{1-10})$-alkenylene and unsubstituted or substituted $(C_{1-10})$-alkenylene where the substituents on $Q^2$ are independently selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and unsubstituted or substituted aryl; and/or
adjacent substituents on $Q^2$ are joined together to form, including the carbon atoms to which they are attached, one or more unsubstituted or substituted 5-20-membered monocyclic, polycyclic, heterocyclic, carbocyclic, saturated, unsaturated or metallocenyl ring systems;
the term substituted with respect to the $Q^2$ substituents means that one or more of the available hydrogen atoms on the group are replaced with $(C_{1-6})$-alkyl, fluoro-substituted $(C_{1-6})$-alkyl, $(C_{1-6})$-alkoxy, fluoro-substituted $(C_{1-6})$-alkoxy, halo or $(C_{6-14})$-aryl; and
$Q^2$ is chiral or achiral.

In another embodiment of the disclosure, $R^5$, $R^6$, $R^7$ and $R^8$ are independently selected from H, $(C_{1-6})$-alkyl, $(C_{3-10})$-cycloalkyl and phenyl, the latter three groups each being optionally substituted with one to five, suitably one to three, substituents independently selected from $(C_{1-4})$-alkyl, fluoro-substituted $(C_{1-4})$-alkyl, halo, $(C_{1-4})$-alkoxy and fluoro-substituted $(C_{1-4})$-alkoxy; $Q^2$ is selected from unsubstituted or substituted $(C_{1-8})$-alkylene where the substituents on $Q^2$ are independently selected from one to five, suitably one to three, of $(C_{1-4})$-alkyl, fluoro-substituted $(C_{1-4})$-alkyl, halo, $(C_{1-4})$-alkoxy, fluoro-substituted $(C_{1-4})$-alkoxy, unsubstituted and substituted phenyl and substituted and unsubstituted naphthyl, or
adjacent substituents are joined together to form, including the carbon atoms to which they are attached, one or more unsubstituted or substituted phenylene, cyclohexylene, naphthylene, pyridylene or ferrocenylene groups; and $Q^2$ is chiral or achiral.

In another embodiment, $R^5$, $R^6$, $R^7$ and $R^8$ are all H or $(C_{1-6})$-alkyl. In another embodiment, $R^5$, $R^6$, $R^7$ and $R^8$ are all H.

In a further embodiment, the optional substituents on $Q^2$ are selected from $(C_{1-4})$-alkyl and substituted or unsubstituted phenyl. In another embodiment, the optional substituents on $Q^2$ are selected from iso-propyl, phenyl and 4-methoxyphenyl.

In another embodiment, the compound of the Formula (II) is

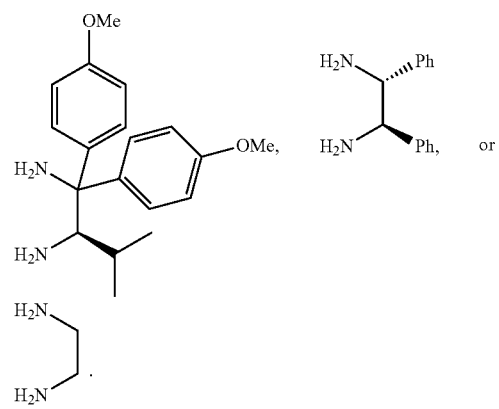

In a further embodiment of the disclosure, the bidentate aminophosphine (P—N) ligand is a compound of the Formula (III)

$$R^9R^{10}P\text{-}Q^3\text{-}NR^{11}R^{12} \qquad (III)$$

wherein $R^9$ and $R^{10}$ are independently as defined for $R^1$-$R^4$ as defined in Formula (I),
$R^{11}$ and $R^{12}$ are independently as defined for $R^5$-$R^8$ as defined in Formula (II), and
$Q^3$ is as defined for $Q^1$ as defined in Formula (I).

In another embodiment of the disclosure, $R^9$ and $R^{10}$ are independently selected from $(C_{1-6})$-alkyl, $(C_{3-10})$-cycloalkyl and phenyl, each group being optionally substituted with one to five, suitably one to three substituents independently selected from $(C_{1-4})$-alkyl, fluoro-substituted $(C_{1-4})$-alkyl, halo, $(C_{1-4})$-alkoxy and fluoro-substituted $(C_{1-4})$-alkoxy.

In another embodiment of the disclosure, $R^{11}$ and $R^{12}$ are all H or one of $R^{11}$ or $R^{12}$ is joined with a substituent on $Q^3$ to form, together with the nitrogen atom to which $R^{11}$ and $R^{12}$ is attached, a substituted or unsubstituted pyridine ring and the other of one of $R^{11}$ or $R^{12}$ is not present.

In another embodiment, the tridentate diaminophosphine (P—N—N) ligand is a compound of the Formula (IV):

$$R^{13}R^{14}P\text{-}Q^4\text{-}NR^{15}\text{-}Q^5\text{-}NR^{16}R^{17} \qquad (IV)$$

wherein
$R^{13}$ and $R^{14}$ are independently as defined for $R^1$-$R^4$ as defined in Formula (I),
$Q^4$ and $Q^5$ are as defined for $Q^1$ as defined in Formula (I),
$R^{15}$ is selected from H, $(C_{1-20})$-alkyl, $(C_{3-20})$-cycloalkyl and $(C_{6-18})$-aryl, the latter three groups each being optionally substituted with one or more substituents independently selected from $(C_{1-6})$-alkyl, fluoro-substituted $(C_{1-6})$-alkyl, halo, $(C_{1-5})$-alkoxy, fluoro-substituted $(C_{1-6})$-alkoxy and $(C_{6-14})$-aryl, or
$R^{15}$ is joined with a substituent on $Q^4$ and/or $Q^5$ to form, together with the nitrogen atom to which $R^{15}$ is attached, a 4- to 10-membered saturated or unsaturated, monocyclic or bicyclic ring system,
$R^{16}$ and $R^{17}$ are independently as defined for $R^5$-$R^8$ as defined in Formula (II).

In another embodiment of the disclosure, $R^{13}$ and $R^{14}$ are independently selected from $(C_{1-6})$-alkyl, $(C_{3-10})$-cycloalkyl and phenyl, each group being optionally substituted with one to five, suitably one to three substituents independently selected from $(C_{1-4})$-alkyl, fluoro-substituted $(C_{1-4})$-alkyl, halo, $(C_{1-4})$-alkoxy and fluoro-substituted $(C_{1-4})$-alkoxy.

In another embodiment of the disclosure, $R^{16}$ and $R^{17}$ are all H or one of $R^{16}$ or $R^{17}$ is joined with a substituent on $Q^5$ to form, together with the nitrogen atom to which $R^{16}$ and $R^{17}$ is attached, a substituted or unsubstituted pyridine ring and the other of one of $R^{16}$ or $R^{17}$ is not present.

In another embodiment, $R^{15}$ is selected from H, $(C_{1-6})$-alkyl, $(C_{3-10}$-cycloalkyl and phenyl, the latter three groups each being optionally substituted with one or more, suitably one to five, suitably one to three, substituents independently selected from $(C_{1-4})$-alkyl, fluoro-substituted $(C_{1-4})$-alkyl halo, $(C_{1-4})$-alkoxy, fluoro-substituted $(C_{1-4})$-alkoxy and phenyl.

In another embodiment, the tridentate diaminophosphine (P—N—P) ligand is a compound of the Formula (V):

$$R^{18}R^{19}P\text{-}Q^6\text{-}NR^{20}\text{-}Q^7\text{-}PR^{21}R^{22} \qquad (V)$$

wherein
$R^{18}$, $R^{19}$, $R^{21}$ and are independently as defined for $R^1$-$R^4$ as defined in Formula (I),
$Q^6$ and $Q^7$ are as defined for $Q^1$ as defined in Formula (I),
$R^{20}$ is as defined as $R^{15}$ as defined in Formula (IV).

In another embodiment of the disclosure, $R^{18}$, $R^{19}$, $R^{21}$ and $R^{22}$ are independently selected from $(C_{1-6})$-alkyl, $(C_{3-10})$-cycloalkyl and phenyl, the latter three groups each being optionally substituted with one to five, suitably one to three substituents independently selected from $(C_{1-4})$-alkyl, fluoro-substituted $(C_{1-4})$-alkyl, halo, $(C_{1-4})$-alkoxy and fluoro-substituted $(C_{1-4})$-alkoxy.

In another embodiment, $R^{20}$ is selected from H, $(C_{1-6})$-alkyl, $(C_{3-10})$-cycloalkyl and phenyl, the latter three groups each being optionally substituted with one to five, suitably one or more substituents independently selected from $(C_{1-4})$-alkyl, fluoro-substituted $(C_{1-4})$-alkyl halo, $(C_{1-4})$-alkoxy, fluoro-substituted $(C_{1-4})$-alkoxy and phenyl.

In another embodiment of the disclosure, the tetradentate diaminodiphosphine (P—N—N—P) ligand is a compound of the Formula (VIa) or (VIb):

$$R^{23}R^{24}P\text{-}Q^8\text{-}NR^{25}\text{-}Q^9\text{-}NR^{26}\text{-}Q^{10}\text{-}PR^{27}R^{28} \qquad (VIa)$$

$$R^{23}R^{24}P\text{-}Q^8\text{=}N\text{-}Q^9\text{-}N\text{=}Q^{10}\text{-}PR^{27}R^{28} \qquad (VIb)$$

wherein $R^{23}$, $R^{24}$, $R^{27}$ and $R^{28}$ are independently as defined for $R^1$ and $R^2$ in Formula (I);
$R^{25}$ and $R^{26}$ are independently as defined for $R^{15}$ in Formula (IV); and
$Q^8$, $Q^9$ and $Q^{10}$ are independently as defined for $Q^1$ in Formula (I).

In another embodiment of the disclosure, $R^{23}$, $R^{24}$, $R^{27}$ and $R^{28}$ are independently selected from $(C_{1-6})$-alkyl, $(C_{3-10})$-cycloalkyl and phenyl, the latter three groups each being optionally substituted with one to five, suitably one to three substituents independently selected from $(C_{1-4})$-alkyl, fluoro-substituted $(C_{1-4})$-alkyl, halo, $(C_{1-4})$-alkoxy and fluoro-substituted $(C_{1-4})$-alkoxy.

In another embodiment, $R^{25}$ and $R^{26}$ are independently selected from H, $(C_{1-6})$-alkyl, $(C_{3-10})$-cycloalkyl and phenyl, the latter three groups each being optionally substituted with one or more, suitably one to five, suitably one to three, substituents independently selected from $(C_{1-4})$-alkyl, fluoro-substituted $(C_{1-4})$-alkyl halo, $(C_{1-4})$-alkoxy, fluoro-substituted $(C_{1-4})$-alkoxy and phenyl.

In another embodiment, the monodentate phosphine (P) ligand is a compound of the Formula (VII):

$$PR^{29}R^{30}R^{31} \qquad (VII)$$

wherein $R^{29}$, $R^{30}$ and $R^{31}$ are independently selected from $(C_{6-18})$-aryl, $(C_{1-20})$-alkyl and $(C_{3-20})$-cycloalkyl, each being optionally substituted with one or more substituents independently selected from $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl, or
$R^{29}$ and $R^{30}$ or $R^{29}$ and $R^{31}$ or $R^{30}$ and $R^{31}$ or $R^{29}$-$R^{31}$ are joined to form, together with the phosphorous atom to which they are attached, a saturated or unsaturated, monocyclic or polycyclic, substituted or unsubstituted ring system containing from 3 to 14 atoms.

In a further embodiment of the disclosure, $R^{29}$, $R^{30}$ and $R^{31}$ are independently selected from phenyl, $(C_{1-6})$-alkyl and $(C_{3-10})$-cycloalkyl, each being optionally substituted with one to five, suitably one to three substituents independently selected from $(C_{1-4})$-alkyl, fluoro-substituted $(C_{1-4})$-alkyl, halo, $(C_{1-4})$-alkoxy and fluoro-substituted $(C_{1-4})$-alkoxy.

In another embodiment, $R^{29}$, $R^{30}$ and $R^{31}$ are all cyclohexyl, phenyl, xylyl or tolyl.

In a further embodiment, the monodentate amino (N) ligand is a compound of the formula (VIII):

$$NR^{32}R^{33}R^{34} \qquad (VIII)$$

$R^{32}$-$R^{34}$ are independently selected from H, $(C_{1-20})$-alkyl, $(C_{3-20})$-cycloalkyl and $(C_{6-18})$-aryl, the latter three groups each being optionally substituted with one or more substituents independently selected from $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl, or $R^{32}$ and $R^{33}$ or $R^{32}$ and $R^{34}$ or $R^{33}$ and $R^{34}$ or $R^{32}$-$R^{34}$ are joined to form, together with the nitrogen atom to which they are attached, a saturated or unsaturated, monocyclic or polycyclic, substituted or unsubstituted ring system containing from 3 to 14 atoms.

In another embodiment of the disclosure, $R^{32}$-$R^{34}$ are independently selected from H, $(C_{1-6})$-alkyl, $(C_{3-10})$-cycloalkyl and phenyl, the latter three groups each being optionally substituted with one to five, suitably one to three, substituents independently selected from $(C_{1-4})$-alkyl, fluoro-substituted $(C_{1-4})$-alkyl, halo, $(C_{1-4}$-alkoxy and fluoro-substituted $(C_{1-4})$-alkyl.

In another embodiment of the present disclosure, the transition metal hydride is selected from

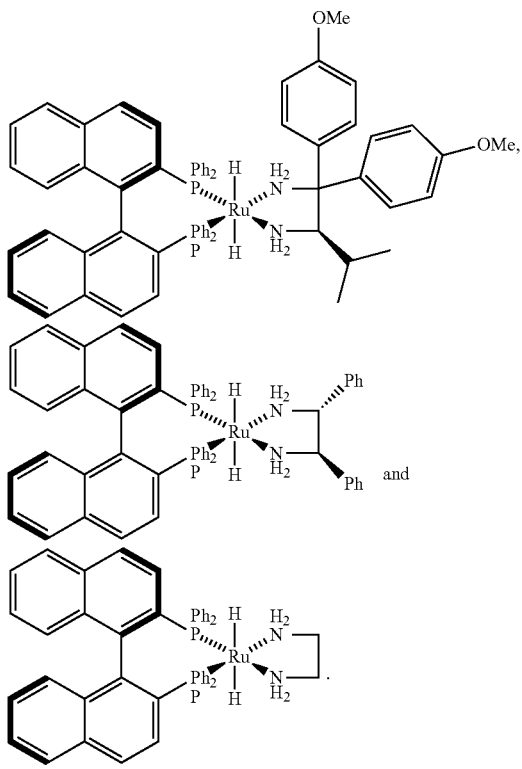

In a further embodiment of the disclosure, the compound comprising one or more imide moieties is a compound of the Formula (IX)

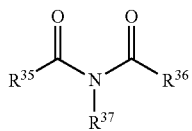

(IX)

wherein
$R^{35}$ and $R^{36}$ are independently selected from $(C_{1-20})$-alkyl, $(C_{3-20})$-cycloalkyl and $(C_{6-18})$-aryl, each group being optionally substituted, wherein the optional substituents are independently selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl and/or one or more of the carbon atoms is optionally replaced with a heteromoiety selected from O, S, N, NH and N—$(C_{1-6})$-alkyl, or $R^{35}$ and $R^{36}$ are joined together to form, including the carbon atoms to which they are attached and the imide nitrogen, an unsubstituted or substituted 5-20-membered monocyclic, polycyclic, heterocyclic, carbocyclic, saturated or unsaturated ring system, wherein the optional substituents are selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl; and $R^{37}$ is selected from H, $(C_{1-6})$-alkyl, $(C_{3-8})$-cycloalkyl and $(C_{6-14})$-aryl, the latter three groups being optionally substituted with one or more of $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl and/or one or more of the carbon atoms is optionally replaced with a heteromoiety selected from O, S, N, NH and N—$(C_{1-6})$-alkyl; and where the compound of Formula (IX) is chiral or achiral.

In another embodiment, the compound of the Formula (IX) is cyclic or acyclic. In another embodiment, the compound of the Formula (IX) is cyclic.

In another embodiment, $R^{35}$ and $R^{36}$ are independently selected from $(C_{1-10})$-alkyl, $(C_3$—O-cycloalkyl and $(C_{6-14})$-aryl, each group being optionally substituted, wherein the optional substituents are independently selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl and/or one or more of the carbon atoms is optionally replaced with a heteromoiety selected from O, S, N, NH and N—$(C_{1-6})$-alkyl.

In another embodiment, $R^{35}$ and $R^{36}$ are independently selected from $(C_{1-6})$-alkyl, $(C_{3-8})$-cycloalkyl and phenyl, each group being optionally substituted, wherein the optional substituents are independently selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl and/or one or more of the carbon atoms is optionally replaced with a heteromoiety selected from O, S, N, NH and N—$(C_{1-6})$-alkyl.

In another embodiment of the disclosure, $R^{35}$ and $R^{36}$ are joined together to form, including the carbon atoms to which they are attached and the imide nitrogen, a polycyclic $(C_{8-12})$-cycloalkyl or $(C_{8-12})$-cycloalkenyl ring system, each being optionally substituted with one to five, suitably one to three, substituents independently selected from $(C_{1-6})$-alkyl, fluoro-substituted $(C_{1-6})$-alkyl, halo, $(C_{1-6})$-alkoxy, fluoro-substituted $(C_{1-6})$-alkoxy and $(C_6)$-aryl, and in which one to five carbon atoms in the polycyclic $(C_{8-12})$-cycloalkyl or $(C_{8-12})$-cycloalkenyl ring system are optionally replaced with a heteroatom selected from O, N, NH, N—$(C_{1-6})$-alkyl and S.

In another embodiment, $R^{35}$ and $R^{36}$ are joined to form, including the carbon atoms to which they are attached and the imide nitrogen, a ring system selected from:

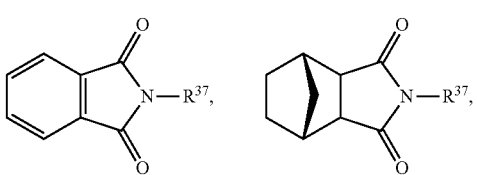

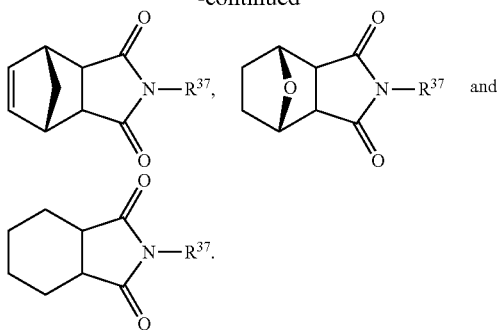

In another embodiment, $R^{37}$ is H, $(C_{1-3})$-alkyl, $(C_{3-6})$-cycloalkyl or phenyl, the latter three groups being optionally substituted, wherein the optional substituents are independently selected from $(C_{1-6})$-alkyl, fluoro-substituted $(C_{1-5})$-alkyl, halo, $(C_{1-6})$-alkoxy, fluoro-substituted $(C_{1-6})$-alkoxy and phenyl. In a further embodiment, $R^{37}$ is H, methyl, ethyl or phenyl the latter three groups being optionally substituted, wherein the optional substituents are independently selected from $(C_{1-4})$-alkyl, fluoro-substituted $(C_{1-4})$-alkyl, halo, $(C_{1-6})$-alkoxy, fluoro-substituted $(C_{1-4})$-alkoxy and phenyl.

It will be understood that the compound of the formula (IX) also includes compound which contain more than one imide moiety, for example, a compound such as

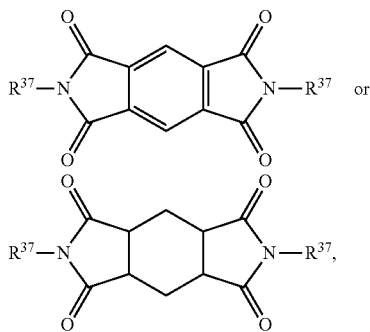

in which $R^{37}$ is the same or different and is as defined above for $R^{37}$ in the compound of formula (IX).

In another embodiment of the present disclosure, the compound of the Formula (IX) is mono-reduced to a compound of the Formula (Xa) or (Xb)

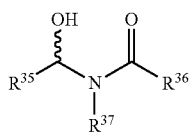

(Xa)

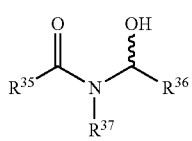

(Xb)

wherein $R^{35}$-$R^{37}$ are as defined for Formula (IX).

In an embodiment, since the compound of the Formula (X) will contain a stereocenter when one of the carbonyl moieties is reduced to the corresponding hydroxy moiety, it is hereby understood that the final product of Formulae (Xa) or (Xb), is chiral, thus possibly consisting of a practically pure enantiomer or of a mixture of stereoisomers, depending on the nature of the catalyst used in the process. Further, in another embodiment, as a result of there being a possible plane of symmetry in a compound of the Formula (IX), the mono-reduction of a compound of Formula (IX) results in the desymmetrization of the compound, providing a very efficient method to produce multiple stereogenic centers with one enantioselective catalytic event, as indicated by the (*) in the structures in a specific embodiment in Scheme 5 below.

Scheme 5

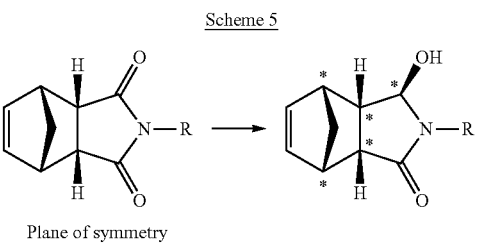

Plane of symmetry

It will be understood by those skilled in the art that if one stereoisomer of a chiral hydride catalyst of the present disclosure produces as a reaction product one enantiomer, or a product mixture having a high enantiomeric excess, the other stereoisomer of the chiral hydride catalyst will produce the as a reaction product the other enantiomer, or a product mixture having a high enantiomeric excess of the other enantiomer.

In another embodiment of the present disclosure, the transition metal hydride catalyst is prepared on a solid support, such as a polymeric solid support. In an embodiment, a ligand (L) of the catalysts of the present disclosure is attached or bonded to a solid support, such as polymeric solid support, for example a polyethylene polymeric solid support, which allows the catalyst to be filtered easily from the reaction mixture. In an embodiment, when the catalyst of the present disclosure is attached or bonded through a ligand (L) to a solid support, the catalyst is easily recycled, for example, by filtering, so that the catalysts can be reused to further catalyze imide mono-reductions.

In another embodiment of the disclosure, there is also provided pre-catalysts, which under appropriate conditions, are converted into the active transition metal hydride catalysts, possessing at least one hydride ligand.

In an embodiment, the neutral monodentate ligand is any neutral two electron donor, such as water, acetonitrile, DMF, ammonia, pyridine, tetrahydrofuran (THF), CO, tBuCN or t-BuNC.

In another embodiment of the disclosure, the anionic monodentate ligand is any anionic two electron donor, such as halo (fluoro, chloro, bromo or iodo), $(C_{1-6})$-alkoxy, hydroxy, $BF_4^-$, $AlH_4^-$, thiocyanate, cyano, carboxylate, sulfonates and nitrates.

In another embodiment, the counteranion is any non-coordinating counter anion, such as $OTf^-$, $BF_4^-$ and $PF_6^-$.

A person skilled in the art will understand the number and type of monodentate ligands and counteranions (monodentate) that will be necessary to form the transition metal hydrides of the present disclosure. This will be dependent upon the identity of the transition metal, the valency requirements of the transition metal and the identity of the (P), (N), (P—P), (N—N), (P—N), (P—N—N), (P—N—P) and (P—N—N—P) ligands which are coordinated to the transition metal.

In another embodiment of the disclosure, the process of mono-reducing one or more imide moieties in a compound comprises contacting the compound with hydrogen gas and a pre-catalyst comprising a transition metal compound under conditions to convert the pre-catalyst to the transition metal hydride, in the presence of a base, under conditions for the mono-reduction of the one or more imide moieties to form a compound comprising one or more hydroxy amides. In another embodiment, the transition metal compound is a complex comprising a suitable transition metal M, and coordinated thereto, one to four, optionally one to three, or one to two, or two, ligands selected from:

(i) a bidentate diphosphine (P—P) ligand,
(ii) a bidentate diamino (N—N) ligand,
(iii) a bidentate aminophosphine (P—N) ligand,
(iv) a tridentate diaminophosphine (P—N—N) ligand,
(v) a tridentate aminodiphosphine (P—N—P) ligand,
(vi) a tetradentate diaminodiphosphine (P—N—N—P) ligand,
(vii) a monodentate phoshine (P) ligand, and
(viii) a monodentate amine ligand (N);

zero to two, optionally zero, or one, or two, neutral monodentate ligands; and zero to two, optionally zero, or one, or two, anionic monodentate ligands, the complex being neutral or cationic, and if the complex is cationic, the complex further comprises one or more suitable counteranions.

In an embodiment, the anionic monodentate ligand is halo, for example, chloro.

In another embodiment, when a pre-catalyst is used for the mono-reduction of imides, the pre-catalyst is converted into a transition metal hydride catalyst, under conditions to form the transition metal hydride catalyst and subsequently for the mono-reduction of an imide containing compound to form a compound comprising one or more hydroxy amides.

In an embodiment, the base is any conventional base and one can cite, as non-limiting examples, organic non-coordinating bases such as DBU, a carbonate salt, such as sodium or potassium carbonate, a carboxylate salt, such as sodium or potassium acetate, an alcoholate salt, such as potassium t-butoxide or sodium or potassium hydroxide, or a silazide salt, such as potassium bis(trimethylsilyl)azide.

In the processes of this disclosure, the catalytic hydrogenation reaction is carried out in the presence of an organic solvent. A wide variety of organic solvents can be used for the catalytic hydrogenation. In another embodiment, the solvent is selected from tetrahydrofuran, diethyl ether, hydrocarbon solvents (hexane or cyclohexane), chlorinated solvents, alcohols (isopropanol or ethanol), toluene, xylene and mixtures thereof.

In another embodiment of the disclosure, the hydrogen gas is used at a pressure in the range of about 1 atm to about 100 atm. In another embodiment of the disclosure, the hydrogen gas is used at a pressure in the range of about 40 atm to about 60 atm. In another embodiment, the hydrogen gas is used at a pressure of about 50 atm.

In another embodiment of the disclosure, the process is performed at a temperature of about −20° C. to about 60° C. In a further embodiment, the process is performed at a temperature of about −20° C. to about 20° C. In a further embodiment, the process is performed at a temperature of about −10° C. to about 20° C. In a further embodiment, the process is performed at a temperature of about −10° C. to about 10° C. In another embodiment, the process is performed at a temperature of 0° C.

In an embodiment, the catalyst of Formula (I) is prepared as described in Hamilton, R. J. et al. J. Am. Chem. Soc., 2005, 127:4152-4153; Hamilton, R. J. et al. J. Am. Chem. Soc, 2006, 128:13700-13701; Hamilton R. J. et al. J. Am. Chem. Soc, 2008, 130:11979-11987; or Takebayashi, S. et al., Organometallics, 2009, 28:2349-2351.

Standard catalytic hydrogenation conditions, as used herein, typically implies the mixture of the imide containing compound of the Formula (VIII) with a transition metal hydride catalyst in the presence of a base, with a solvent, and then treating such a mixture with a hydrogen gas at a chosen pressure and temperature.

The transition metal hydride catalyst can be added to the reaction medium in a large range of concentrations. As non-limiting examples, one can cite as catalyst concentration values ranging from about 0.1 mol % to about 10 mol %, based on the amount of substrate to be reduced.

The base may be comprised in a relatively large range. One can cite, as non-limiting examples, ranges between about 1 mol % to about 10 mol %, based on the amount of substrate to be reduced.

The following non-limiting examples are illustrative of the present disclosure:

EXAMPLES

All pressure reactions were carried out in a stainless steel autoclave equipped with a stirring bar. Deuterated solvents were obtained from Cambridge Isotope Laboratories. Common solvents were distilled over appropriate drying reagents. THF was distilled over sodium/benzophenone before each experiment. 2-PrOH, toluene, and $CH_2Cl_2$ were distilled over $CaH_2$. Common chemicals were obtained from Aldrich, TCI America, and Strem, and were used as received unless stated otherwise. Potassium tert-butoxide (KO$^t$Bu) was sublimed before use. Ethylenediamine was distilled over KOH. N-methylsuccinimide was purchased from Aldrich, and used as received. All other imides were prepared by the condensation of corresponding acid anhydrides and amines. All imides were passed through 230-400 mesh silica gel using appropriate solvents, and recrystallized from appropriate solvents. Indene was purchased from Matheson Coleman & Bell, and fractionally distilled. Hydrogen gas was ultra high purity grade purchased from Praxair. $^1H$, $^{13}C$, and $^{31}P$ NMR spectra were taken using Varian Inova (400 MHz) and Varian DirectDrive (500 MHz) spectrometers. $^1H$ and $^{13}C$ NMR chemical shifts are reported in parts per million (δ) relative to TMS with the solvent as the internal reference. $^{31}P$ chemical shifts are reported in parts per million (δ) relative to 85% $H_3PO_4$ as the external reference. $^{19}F$ chemical shifts are reported in parts per million (δ) relative to $CCl_3F$ as the external reference. NMR peak assignments were made using gCOSY, and $^{13}C$-$^1H$ gHSQC NMR experiments. Abbreviations for NMR spectra are s (singlet), d (doublet), t (triplet), q (quartet), dd (doublet of doublet), ddd (doublet of doublet of doublet), dt (doublet of triplet), tt (triplet of triplet) m (multiplet), and br (broad). IR spectra were taken using a Nic-Plan FTIR microscope, and are reported in frequency of absorption (cm$^{-1}$). High resolution mass spectra were taken using an Applied BioSystems Mariner BioSpectrometry Workstation oaTOF mass spectrometer. Elemental analysis data were obtained using a Carlo Erba CHNS-O EA1108 elemental analyzer. Optical rotations ([α]$_D^{23}$) were measured using a Perkin Elmer 241 polarimeter. Melting points (M.p.) were measured using a Perkin Elmer Pyris 1 differential scanning calorimeter. HPLC analysis was performed using a Waters 600E multisolvent delivery system equipped with a Waters 715 Ultra WISP sample processor, Waters temperature control system, Waters 990 photodiode array detector, Waters 410 differential refractometer, Waters 5200 printer plotter, and Daicel CIRALPAK IB (4.6 mm i.d.×250 mm) chiral column. HPLC-grade hexanes (min. 99.5%) and 2-propanol (min. 99.7%) were obtained from Caleclon Laboratories Ltd.

Example 1

General Preparation of Catalysts

Ru((R)-BINAP)(diamine)(H)$_2$

A solution of [Ru((R)-BINAP)((1-5-η)-C$_8$H$_{11}$)]BF$_4$ (9.2 mg, 0.010 mmol) in THF (0.50 mL) was shaken under H$_2$ (~2 atm) in an NMR tube at 0° C. for 3 min. The resulting solution containing [Ru((R)-BINAP)(H)(THF)$_3$]BF$_4$ was then cooled in a −78° C. dry ice/acetone bath, and the diamine (0.010 mmol) in THF (0.20 mL) was added by cannula under H$_2$ pressure (~2 atm) at −78° C. The NMR tube was shaken for about 5 sec outside the −78° C. bath, and then returned to the bath. This process was repeated nine times. KO$^t$Bu (5.6 mg, 0.050 mmol) in THF (0.30 mL) was then added by cannula under H$_2$ pressure (~2 atm). The NMR tube was shaken for about 5 sec outside the −78° C. bath and returned to the bath. This process was repeated nine times. The solution color changed from yellow to red during the addition of KO$^t$Bu to form a mixture containing [Ru((R)-BINAP)(diamine)(H)$_2$] and 4 equiv KO$^t$Bu. This mixture can be used directly for catalytic hydrogenation of imides.

Example 2

General Hydrogenation of Imide

A solution of the imide (1.00 mmol) in THF (7 mL), prepared under argon, was added to a stainless steel autoclave equipped with a magnetic stir bar. The atmosphere in the autoclave was then flushed with H$_2$ gas for about 3 min, and a solution of trans-[Ru((R)-BINAP)(diamine)(H)$_2$] (0.010 mmol) and KO$^t$Bu (0.040 mmol) in THF (1.0 mL), prepared typically as described in Example 1, was then added by cannula under H$_2$ pressure. The autoclave was then pressurized with H$_2$ to 50 atm, and the reaction mixture stirred at 0° C. under 50 atm H$_2$ for 6 h. The autoclave was then vented slowly at 0° C., and the reaction yield, enantiomeric excess and diastereomeric ratio (d.r.) was determined by $^1$H NMR and HPLC.
Hydroxy-Lactams (Formula (X))

4a:

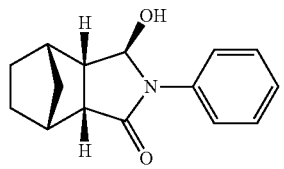 [SMILES: O=C1[C@@H]2[C@@H]3CC[C@@H](C3)[C@@H]2[C@@H](O)N1c1ccccc1]

$^1$H NMR (399.79 MHz, CDCl$_3$, 27.0° C.): δ 1.3-1.6 (6H, m, 3CH$_2$), 2.45 (1H, ddd, J=1.1, 4.9 and 10.5 Hz, CH), 2.57 (1H, br t, J=3.8 Hz, bridgehead CH), 2.71 (1H, br, bridgehead CH), 3.03 (1H, dd, J=5.5 and 10.5 Hz, CH), 3.28 (1H, d, J=8.3 Hz, OH), 5.33 (1H, d, J=7.3 Hz, CHOH), 7.24 (1H, m, aromatic CH), 7.36 (2H, m, aromatic 2CH), 7.48 (2H, m, aromatic 2CH). $^{13}$C{$^1$H} NMR (100.5 MHz, CDCl$_3$, 27.0° C.): δ 22.9 (CH$_2$), 24.8 (CH$_2$), 39.5 (bridgehead CH), 39.9 (bridgehead CH), 41.2 (CH$_2$), 48.07 (CH), 48.10 (CH) 86.0 (CHOH), 124.0 (aromatic), 126.4 (aromatic), 129.1 (aromatic), 137.2 (aromatic), 175.9 (C=O). IR (CHCl$_3$ cast film): 3347, 2960, 2881, 1673, 1597, 1500, 1409, 1066, 759 cm$^{-1}$. HRMS (ESI$^+$) m/z calcd for C$_{15}$H$_{17}$NNaO$_2$$^+$ ([M+Na]$^+$): 266.11515. Found: 266.11509. Elemental analysis calcd for C$_{15}$H$_{17}$NO$_2$: N, 5.76; C, 74.05; H, 7.04. Found: N, 5.61; C, 74.04; H, 7.49. [α]$_D^{23}$ −113.73 (c=1.00 g/100 mL of CHCl$_3$, 93% ee). M.p.: 153.5° C. HPLC analysis conditions: Daicel CHIRALPAK IB column (4.6 mm i.d.×250 mm), Hexanes: 2-Propanol=97:3, 30° C., flow rate=0.8 mL/min, detection (UV, 210 nm). Retention times: 27.8 min (minor enantiomer), 39.1 min (major enantiomer).

4b:

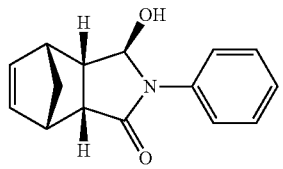 [SMILES: O=C1[C@H]2[C@@H]([C@@H](O)N1c1ccccc1)[C@H]1C=C[C@@H]2C1]

$^1$H NMR (399.79 MHz, acetone-d$_6$, 27.0° C.): δ 1.47 (2H, m, CH$_2$), 2.76 (1H, m, CH), 3.21 (3H, overlapping multiplet, CH and bridgehead 2CH), 5.04 (1H, d, J=8.1 Hz, CHOH), 5.23 (1H, d, J=8.7 Hz, OH), 6.08 (1H, dd, J=2.8 and 5.6 Hz, CH), 6.19 (1H, dd, J=2.8 and 5.6 Hz, CH), 7.12 (1H, m, aromatic CH), 7.28 (2H, m, aromatic 2CH), 7.50 (2H, m, aromatic 2CH). $^{13}$C{$^1$H} NMR (100.5 MHz, ~0.7 mL of acetone-d$_6$ with ~0.1 mL of MeOH-d$_a$, 27.0° C.): δ 46.0 (bridgehead CH), 46.5 (bridgehead CH), 47.5 (CH), 50.4 (CH), 51.7 (CH$_2$), 87.5 (CHOH), 125.3 (aromatic), 126.7 (aromatic), 129.4 (aromatic), 134.7 (aromatic), 136.6 (C=C), 138.9 (C=C), 176.1 (C=O). IR (CHCl$_3$ cast film): 3187, 2968, 1666, 1594, 1502, 1428, 1330, 1228, 1076, 721 cm$^{-1}$. HRMS (ESI$^+$) m/z calcd for C$_{15}$H$_{15}$NNaO$_2$$^+$ ([M+Na]$^+$): 264.0995. Found: 264.09938. Elemental analysis calcd for C$_{15}$H$_{15}$NO$_2$: N, 5.81; C, 74.67; H, 6.27. Found: N, 5.86; C, 74.8; H, 6.11. [α]$_D^{23}$ −168.65 (c=1.00 g/100 mL of methanol, >99% ee). M.p.: 120.5° C. HPLC analysis conditions: Daicel CHIRALPAK IB column (4.6 mm i.d.×250 mm), Hexanes: 2-Propanol=97:3, 30° C., flow rate=0.8 mL/min, detection (UV, 210 nm). Retention times: 41.1 min (minor enantiomer), 49.7 min (major enantiomer). Product with >99% ee was obtained upon single recrystallization from hot ethanol. Yield after single recrystallization (recrystallization conditions not optimized): 73%.

4c

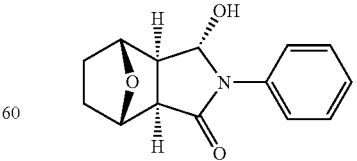

$^1$H NMR (399.79 MHz, CDCl$_3$, 27.0° C.): δ 1.36 (2H, m, CH$_2$), 1.55 (2H, m, CH$_2$), 2.22 (1H, dd, J=0.9 and 7.9 Hz, CH), 2.72 (1H, d, J=7.9 Hz, CH), 4.48 (1H, d, J=4.8 Hz, bridgehead CH), 4.57 (1H, d, J=4.8 Hz, bridgehead CH), 5.02 (1H, br, OH), 5.21 (1H, d, J=1.0 Hz, CHOH), 7.00 (1H, m, aromatic CH), 7.12 (2H, m, aromatic 2CH), 7.29 (2H, m, aromatic 2CH). $^{13}C\{^1H\}$ NMR (100.5 MHz, acetone-$d_6$, 27.0° C.): δ 29.0 ($CH_2$), 29.1 ($CH_2$), 50.9 (CH), 53.4 (CH), 79.8 (bridgehead CH), 81.6 (bridgehead CH) 88.9 (CHOH), 124.3 (aromatic), 126.3 (aromatic), 129.3 (aromatic), 138.9 (aromatic), 174.0 (C=O). IR ($CHCl_3$ cast film): 3315, 2982, 2957, 1658, 1599, 1502, 1419, 1314, 1284, 1056, 747 $cm^{-1}$. HRMS (ESI$^+$) m/z calcd for $C_{14}H_{15}NNaO_3^+$ ([M+Na]$^+$): 268.09441. Found: 268.09411. Elemental analysis calcd for $C_{14}H_{15}NO_3$: N, 5.71; C, 68.56; H, 6.16. Found: N, 5.69; C, 68.54; H, 6.30. $[α]_D^{23}$ −133.33 (c=1.00 g/100 mL of methanol, 87% ee). M.p.: 178.2° C. HPLC analysis conditions: Daicel CHIRALPAK IB column (4.6 mm i.d.×250 mm), Hexanes: 2-Propanol=95:5, 30° C., flow rate=1.0 mL/min, detection (UV, 210 nm). Retention times: 38.9 min (minor enantiomer), 46.6 min (major enantiomer).

4d:

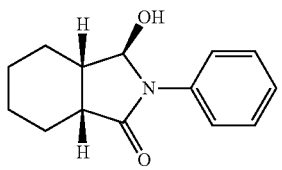 [SMILES: O=C1[C@@H]2CCCC[C@@H]2[C@@H](O)N1c1ccccc1]

$^1H$ NMR (399.79 MHz, $CDCl_3$, 27.0° C.): δ 1.12 (3H, m, $CH_2$), 1.55 (3H, m, $CH_2$), 1.86 (1H, m, $CH_2$), 2.17 (1H, m, $CH_2$), 2.28 (1H, dt, J=6.4 and 11.3 Hz, CH), 2.99 (1H, m, CH), 3.47 (1H, br d, J=5.9 Hz, OH), 5.10 (1H, d, J=4.6 Hz, CHOH), 7.18 (1H, m, aromatic CH), 7.35 (2H, m, aromatic 2CH), 7.54 (2H, m, aromatic 2CH). $^{13}C\{^1H\}$ NMR (100.5 MHz, $CDCl_3$, 27.0° C.): δ 22.8 ($CH_2$), 23.0 ($CH_2$), 23.4 ($CH_2$), 26.5 ($CH_2$), 39.5 (CH), 41.1 (CH), 88.5 (CHOH), 122.3 (aromatic), 125.6 (aromatic), 129.0 (aromatic), 138.2 (aromatic), 175.6 (C=O). IR ($CHCl_3$ cast film): 3315, 2935, 2855, 1666, 1599, 1501, 1409, 1060, 759 $cm^{-1}$. HRMS (ESI$^+$) m/z calcd for $C_{14}H_{17}NNaO_2^+$ ([M+Na]$^+$): 254.11515. Found: 254.11489. Elemental analysis calcd for $C_{14}H_{17}NO_2$: N, 6.06; C, 72.70; H, 7.41. Found: N, 6.01; C, 72.85; H, 7.56. $[α]_D^{23}$ −34.07 (c=1.00 g/100 mL, $CHCl_3$, 93% ee). M.p.: 133.8° C. HPLC analysis conditions: Daicel CHIRALPAK IB column (4.6 mm i.d.×250 mm), Hexanes: 2-Propanol=97:3, 30° C., flow rate=0.8 mL/min, detection (UV, 210 nm). Retention times: 27.0 min (minor enantiomer), 50.8 min (major enantiomer).

4e:

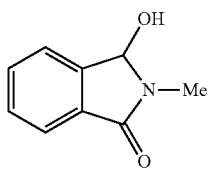 [SMILES: CN1C(=O)c2ccccc2C1=O]

$^1H$ NMR (399.79 MHz, $CDCl_3$, 27.0° C.): δ 2.94 (3H, s, $CH_3$), 3.66 (1H, br, OH), 5.61 (1H, s, CH), 7.42 (1H, m, aromatic CH), 7.60 (3H, m, aromatic 3CH).

4f:

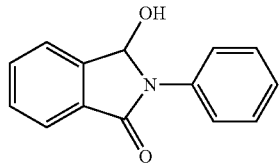 [SMILES: O=C1c2ccccc2C(=O)N1c1ccccc1]

$^1H$ NMR (399.79 MHz, $CDCl_3$, 27.0° C.): δ 3.25 (1H, br, OH), 6.38 (1H, br, CH), 7.22 (1H, m, aromatic CH), 7.4-7.8 (8H, m, aromatic 8CH).

4g:

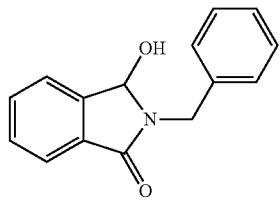 [SMILES: O=C1c2ccccc2C(=O)N1Cc1ccccc1]

$^1H$ NMR (399.79 MHz, $CDCl_3$, 27.0° C.): δ 3.43 (1H, d, J=12.0 Hz, OH), 4.27 (1H, d, J=14.8 Hz, $CH_2$), 4.89 (1H, d, J=14.8 Hz, $CH_2$), 5.60 (1H, d, J=11.6 Hz, CH), 7.2-7.6 (8H, m, aromatic 8CH), 7.69 (1H, m, aromatic CH).

4h:

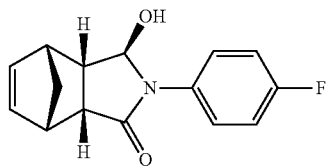 [SMILES: O=C1[C@@H]2[C@H](C(=O)N1c1ccc(F)cc1)[C@@H]1C=C[C@H]2C1]

$^1H$ NMR (399.80 MHz, acetone-$d_6$, 27.0° C.): δ 1.44 (1H, br dt, J=1.6 and 8.4 Hz, $CH_2$), 1.50 (1H, dt, J=1.6 and 8.4 Hz, $CH_2$), 2.76 (1H, m, CH), 3.18 (1H, m, CH), 3.23 (2H, overlapping multiplet, CH and bridgehead CH), 5.00 (1H, d, J=8.0 Hz, CHOH), 5.26 (1H, d, J=8.8 Hz, OH), 6.09 (1H, dd, J=3.2 and 5.6 Hz, CH), 6.20 (1H, dd, J=3.2 and 5.6 Hz, CH), 7.05 (2H, m, aromatic 2CH), 7.50 (2H, m, aromatic 2CH). $^{13}C\{^1H\}$ NMR (100.5 MHz, acetone-$d_6$, 27.0° C.): δ 46.0 (bridgehead CH), 46.5 (bridgehead CH), 47.4 (CH), 50.0 (CH), 51.6 ($CH_2$), 87.2 (CHOH), 115.6 (aromatic), 115.8 (aromatic), 126.4 (aromatic), 126.5 (aromatic), 134.5 (C=C), 136.6 (C=C), 159.7 (aromatic), 162.1 (aromatic), 174.8 (C=O). $^{19}F$ NMR (376.15 MHz, acetone-$d_6$, 27.0° C.): 6-119.27 (tt, J=5.3 and 8.3 Hz). IR (methanol cast film): 3219, 2975, 1667, 1514, 1436, 1254, 1074 $cm^{-1}$. HRMS (ESI$^+$) m/z calcd for $C_{15}H_{14}FNNaO_2^+$ ([M+Na]$^+$): 282.0901. Found: 282.0899. Elemental analysis calcd for $C_{15}H_{14}FNO_2$: N, 5.40; C, 69.49; H, 5.44. Found: N, 5.42; C, 69.47; H, 5.45. $[α]_D^{23}$ −151.13 (c=1.00 g/100 mL of methanol, >99% ee). M.p.: 219.0° C. HPLC analysis conditions: Daicel CHIRALPAK IB column (4.6 mm i.d.×250 mm), Hexanes: 2-Propanol=97:3, 30° C., flow rate=0.8 mL/min, detection (UV, 210 nm). Retention times: 28.1 min (minor enantiomer), 31.5 min (major enantiomer). Product with >99% ee was obtained upon single recrystallization from hot ethyl acetate.

4i:

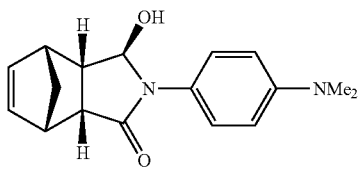 [SMILES: CN(C)c1ccc(N2C(=O)[C@@H]3[C@H](C2=O)[C@@H]2C=C[C@H]3C2)cc1]

$^1$H NMR (399.79 MHz, CDCl$_3$, 27.0° C.): δ 1.44 (1H, m, CH$_2$), 1.61 (1H, dt, J=1.6 and 8.4 Hz, CH$_2$), 2.71 (1H, ddd, J=1, 4.2, and 8.6 Hz, CH), 2.86 (1H, br, CHOH), 2.93 (6H, s, 2CH$_3$), 3.23 (1H, br, CH), 3.28 (1H, m, CH), 3.35 (1H, br, CH), 4.84 (1H, d, J=5.6 Hz, CHOH), 6.16 (1H, dd, J=2.8 and 5.6 Hz, CH), 6.24 (1H, dd, J=2.8 and 5.6 Hz, CH), 6.72 (2H, d, J=8.4 Hz, aromatic 2CH), 7.14 (2H, d, J=8.8 Hz, aromatic 2CH). $^{13}$C{$^1$H} NMR (125.27 MHz, ~0.7 mL of CDCl$_3$ with ~0.1 mL of MeOH-d$_4$, 27.0° C.): δ 40.5 (CH$_3$), 44.9 (bridgehead CH), 45.3 (bridgehead CH), 46.3 (CH), 49.2 (CH), 51.1 (CH$_2$), 87.6 (CHOH), 112.8 (aromatic), 126.0 (aromatic), 126.5 (aromatic), 133.3 (C=C), 136.0 (C=C), 149.5 (aromatic), 176.1 (C=O). IR (CHCl$_3$ cast film): 3332, 3001, 1661, 1565, 1320, 1227, 1067, 801, 758 cm$^{-1}$. HRMS (ESI$^+$) m/z calcd for C$_{17}$H$_{21}$N$_2$O$_2$$^+$ ([M+H]$^+$): 285.1598. Found: 285.1592. Elemental analysis calcd for C$_{17}$H$_{20}$N$_2$O$_2$: N, 9.85; C, 71.81; H, 7.09. Found: N, 9.56; C, 71.41; H, 6.80. [α]$_D^{23}$ −147.69 (c=0.50 g/100 mL of MeOH, 97% ee). M.p.: 237.13° C. HPLC analysis conditions: Daicel CHIRALPAK IB column (4.6 mm i.d.×250 mm), Hexanes:2-Propanol=92:8, 30° C., flow rate=1.6 mL/min, detection (UV, 210 nm). Retention times: 28.1 min (minor enantiomer), 31.1 min (major enantiomer).

4j:

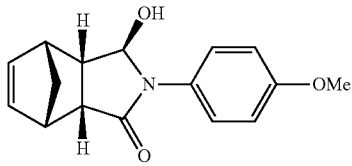 [SMILES: COc1ccc(N2C(=O)[C@@H]3[C@H](C2=O)[C@@H]2C=C[C@H]3C2)cc1]

$^1$H NMR (399.79 MHz, CDCl$_3$, 27.0° C.): δ 1.43 (1H, d, J=8.4 Hz, CH$_2$), 1.61 (1H, d, J=8.4 Hz, CH$_2$), 2.71 (1H, dd, J=4.2 and 8.6 Hz, CH), 3.05 (1H, br, CHOH), 3.23 (1H, br, CH), 3.28 (1H, m, CH), 3.34 (1H, br, CH), 3.78 (3H, s, CH$_3$), 4.83 (1H, s, CHOH), 6.14 (1H, dd, J=2.8 and 5.6 Hz, CH), 6.23 (1H, dd, J=2.8 and 5.6 Hz, CH), 6.86 (2H, m, aromatic 2CH), 7.20 (2H, m, aromatic 2CH). $^{13}$C{$^1$H} NMR (125.69 MHz, CDCl$_3$, 27.0° C.): δ 45.1 (bridgehead CH), 45.6 (bridgehead CH), 46.3 (CH), 49.2 (CH), 51.3 (CH$_2$), 55.5 (CH$_3$), 87.3 (CHOH), 114.4 (aromatic), 126.6 (aromatic), 129.7 (aromatic), 133.2 (C=C), 136.6 (C=C), 158.3 (aromatic), 175.0 (C=O). IR (CHCl$_3$ cast film): 3194, 2976, 1644, 1514, 1249, 1069, 1035, 829, 727 cm$^{-1}$. HRMS (ESI$^+$) m/z calcd for C$_{16}$H$_{17}$NNaO$_3$$^+$ ([M+Na]): 294.1101. Found: 294.1099. Elemental analysis calcd for C$_{16}$H$_{15}$NO$_3$: N, 5.20; C, 71.36; H, 5.61. Found: N, 5.03; C, 70.88; H, 6.22. [α]$_D^{23}$ −151.93 (c=0.50 g/100 mL of MeOH, 95% ee). M.p.: 205.62° C. HPLC analysis conditions: Daicel CHIRALPAK IB column (4.6 mm i.d.×250 mm), Hexanes:2-Propanol=97:3, 30° C., flow rate=0.8 mL/min, detection (UV, 210 nm). Retention times: 82.68 min (minor enantiomer), 112.85 min (major enantiomer).

Discussion

As seen in Tables 1-3, the transition metal hydride catalysts of the present application are capable of mono-reducing imide containing compounds of the Formula (IX) with high yields and enantioselectivities. The yields and selectivities are dramatically higher than those reported in literature reports of imide hydrogenations. The predominant stereochemistry of the hydroxyl group (typically >90%) is trans, resulting from rapid, reversible tautomerization of the hydrogenation product in the presence of a base. Using the Noyori catalysts 5 and 6 (structures at bottom of table), it was found that the enantioselectivities were typically >90%. All the ee's were confirmed by running the racemic mixture under the same conditions in our laboratories. The direduced product was barely detectable by NMR in the product mixtures from these reactions.

The absolute configuration of the compounds produced in Example 2 (compounds 4a-4-j) was not determined, and accordingly, the enantiomers shown in Tables 1-3 may be the opposite enantiomer from what is shown. However, the reactions did produce a single enantiomer with enantiomeric excess as shown in Table 1-3. A person skilled in the art would readily be able to determine the absolute configuration of the compounds produced using methods well known in the art.

Example 3

Intermolecular Cyclization Using Hydroxy Lactam

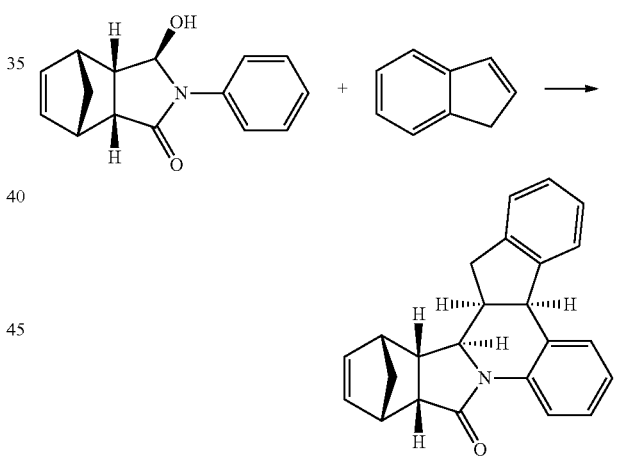

Under argon, γ-hydroxy lactam 4b (>99% ee) (95.8 mg, 0.40 mmol), indene (0.05 mL, 0.43 mmol), and 10 mL of toluene were taken into a 50 mL Schlenk flask equipped with a stirring bar. 4b was scarcely soluble in toluene. BF$_3$.OEt$_2$ (0.1 mL, 0.79 mmol) was then added to the flask at 23° C. Dissolution of 4b was observed as soon as BF$_3$.OEt$_2$ was added. The clear faint yellow solution was stirred for 30 min at 23° C. The reaction was quenched by addition of sat. NaHCO$_3$ (5 mL) at 23° C., followed by stirring at 23° C. for 5 min. Faint yellow solution became colorless upon quenching. The reaction mixture was extracted using CH$_2$Cl$_2$ (100 mL), dried over MgSO$_4$, and concentrated under vacuum. Resulting colorless oil was analyzed by $^1$H NMR and HPLC to determine yield, diastereomeric ratio, and enantiomeric excess. Crystals of major diastereomer was formed upon slow evaporation of ethyl acetate solution. This crystal was used for X-ray diffraction analysis. Yield: 90% (based on $^1$H NMR). Diastereomeric ratio: 91:9 (based on $^1$H NMR). Enantiomeric excess: >99%. $^1$H NMR (399.79 MHz, CDCl$_3$, 27.0° C.): δ 1.47 (1H, d, J=8.4 Hz, CH$_2$), 1.66 (1H, dt, J=1.6 and 8.4 Hz, CH$_2$), 2.75 (1H, m, CH), 2.87 (1H, dd, J=10.6 and 15.4 Hz, CH$_2$), 3.02 (1H, dd, J=8.2 and 15.4 Hz, CH$_2$), 3.19 (1H, br m, bridgehead CH), 3.21-3.30 (2H, m, 2CH), 3.41 (1H, br m, bridgehead CH), 3.60 (1H, t, J=3.0 Hz, CH), 4.46 (1H, d, J=8.8 Hz, CH), 6.17 (1H, dd, J=3.2 and 5.6 Hz, CH), 6.35 (1H, dd, J=3.2 and 5.6 Hz, CH), 7.04 (1H, m, aromatic CH), 7.14 (4H, m, aromatic 4CH), 7.47 (2H, m, aromatic 2CH), 8.01 (1H, dd, J=1.4 and 8.2 Hz, aromatic CH). $^{13}$C{$^1$H} NMR (100.5 MHz, CDCl$_3$, 27.0° C.): δ 32.1 (benzylic CH$_2$), 40.0 (CH), 45.5 (CH), 45.7 (bridgehead CH), 46.1 (bridgehead CH), 46.8 (CH), 51.0 (CH$_2$), 51.1 (CH), 60.8 (CHN), 121.3 (aromatic), 124.8 (aromatic), 124.9 (aromatic), 125.0 (aromatic), 126.4 (aromatic), 126.8 (aromatic), 127.3 (aromatic), 128.6 (aromatic), 130.1 (aromatic), 134.3 (C=C), 135.2 (aromatic), 136.8 (C=C), 141.8 (aromatic), 145.4 (aromatic), 173.3 (C=O). IR (CHCl$_3$ cast film): 2981, 1683, 1492, 1397, 755 cm$^{-1}$. HRMS (ESI$^+$) m/z calcd for C$_{24}$H$_{22}$NO ([M+H]$^+$): 340.1696. Found: 340.1701. Elemental analysis calcd for C$_{24}$H$_{21}$NO: N, 4.13; C, 84.92; H, 6.24. Found: N, 3.92; C, 84.12; H, 6.30. [α]$_D^{23}$ 124.76 (c=1.00 g/100 mL of CHCl$_3$, >99% ee). M.p.: 211.2° C. HPLC analysis conditions: Daicel CHIRALPAK IB column (4.6 mm i.d.×250 mm), Hexanes: 2-Propanol=97:3, 30° C., flow rate=0.8 ml/min, detection (UV, 210 nm). Retention times: 19.7 min (minor enantiomer), 24.7 min (major enantiomer). An X-ray crystallographic structure of the reaction product is shown in FIG. 1.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Yields and Enantioselectivities of the Catalytic Mono-reduction of Imides

| Entry | Compound of the Formula (IX) | Catalyst/Condition (5 or 6) | Compound of the Formula (X) | Yield, E.e. and d.r. |
|---|---|---|---|---|
| 1 | (structure) | 5 (1 mol %); KO$^t$Bu (10 mol %); THF, 0° C.; 50 atm H$_2$, 16 h | (structure) | 88% yield 87% ee d.r. 94:6 |
| 2 | (structure) | 5 (1 mol %); KO$^t$Bu (5 mol %); THF, 0° C.; 50 atm H$_2$, 2 h | (structure) | 81% yield 97% ee d.r. 99:1 |
| 3 | (structure) | 5 (0.1 mol %); KO$^t$Bu (1 mol %); THF, 0° C.; 50 atm H$_2$, 17 h | (structure) | 98% yield 96% ee d.r. 99:1 |
| 4 | (structure) | 6 (1 mol %); KO$^t$Bu (5 mol %); THF, 0° C.; 50 atm H$_2$, 6 h | (structure) | 97% yield 92% ee d.r. 93:7 |
| 5 | (structure) | 5 (1 mol %); KO$^t$Bu (10 mol %); THF, 0° C.; 50 atm H$_2$, 4 h | (structure) | 95% yield 90% ee d.r. 98:2 |

TABLE 1-continued

Yields and Enantioselectivities of the Catalytic Mono-reduction of Imides

| Entry | Compound of the Formula (IX) | Catalyst/Condition (5 or 6) | Compound of the Formula (X) | Yield, E.e. and d.r. |
|---|---|---|---|---|

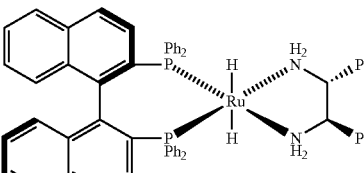

TABLE 2

Hydrogenation of Phthalamides

Imide + $H_2$ (4 atm) $\xrightarrow{\text{1 mol % cat.} \atop \text{9 mol % KO}^t\text{Bu}}$ 4 + 8
THF, 30° C., 3 h

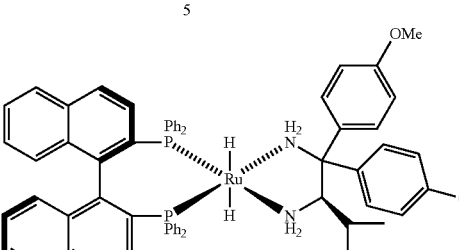

| entry | catalyst | Compound of Formula (IX) | 4 (%)[a] | 8 (%)[a] |
|---|---|---|---|---|
| 1 | 7 | N—Me phthalimide | 70 | 0 |
| 2[b] | 7 | N-phenyl phthalimide | 76 | 0 |
| 3 | 7 | N-benzyl phthalimide | 66 | 0 |
| 4 | 5 | N—Me phthalimide | 55 | 0 |

TABLE 2-continued

Hydrogenation of Phthalamides

Imide + H$_2$ (4 atm) $\xrightarrow[\text{THF, 30° C., 3 h}]{\text{1 mol \% cat.} \atop \text{9 mol \% KO}^t\text{Bu}}$ 4 + 8

| entry | catalyst | Compound of Formula (IX) | 4 (%)[a] | 8 (%)[a] |
|---|---|---|---|---|
| 5[c] | 5 | N-methylphthalimide | 30 | 20 |
| | 7 | Ru complex with BINAP-type ligand and diamine | | |

[a] Determined by $^1$H NMR.
[b] In THF/CH$_2$Cl$_2$ = 2:1 due to solubility of imide.
[c] At 60° C.

TABLE 3

Enantioselective hydrogenation of meso-imides[a]

| entry | Compound of Formula (IX) | T (° C.) | time (h) | 4 (%)[b] | 8 (%)[b] | d.r. of 4[b] | e.e. of 4 (%)[c] |
|---|---|---|---|---|---|---|---|
| 1[d] | N-phenyl norbornene imide | 23 | 3 | 70 | 12 | >99:1 | 83 |
| 2 | N-(4-F-phenyl) norbornene imide | 0 | 17 | 99 | 0 | >99:1 | 97 |
| 3 | N-(4-NMe$_2$-phenyl) norbornene imide | 0 | 17 | 92 | 0 | >99:1 | 97 |
| 4 | N-(4-OMe-phenyl) norbornene imide | 0 | 17 | 98 | 0 | >99:1 | 95 |

TABLE 3-continued

Enantioselective hydrogenation of meso-imides[a]

| entry | Compound of Formula (IX) | T (° C.) | time (h) | 4 (%)[b] | 8 (%)[b] | d.r. of 4[b] | e.e. of 4 (%)[c] |
|---|---|---|---|---|---|---|---|
| 5[e] | 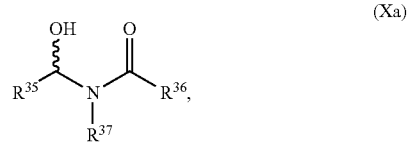 | 0 | 57 | 90 | trace | 97:3 | 90 |
| 6 | 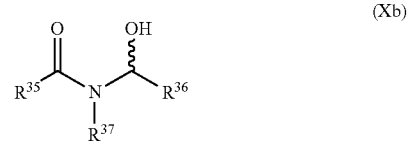 | 0 | 17 | 44 | 0 | >99:1 | 92 |

[a]Imide/5/KO$^t$Bu = 500:1:9, 50 atm H$_2$ in THF unless otherwise noted.
[b]Determined by $^1$H NMR.
d.r.: diastereomeric ratio.
[c]Determined by HPLC analysis using Daicel CHIRLPAK IB column.
[d]Imide/5/KO$^t$Bu = 100:1:4.
[e]imide/5/KO$^t$Bu = 1000:1:99.

We claim:

1. A process for the mono-reduction of one or more imide moieties in a compound comprising contacting the compound with hydrogen gas and a catalyst comprising a transition metal hydride in the presence or absence of a base, under conditions for the mono-reduction of the one or more imide moieties to form a compound comprising one or more hydroxy amides, wherein mono-reduction comprises a single reduction of one carbonyl functionality of an imide moiety to a hydroxy group to form a hydroxy amide, wherein:

(i) said compound comprising one or more imide moieties is a compound of Formula (IX)

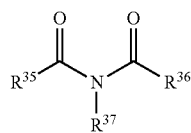

(IX)

wherein $R^{35}$ and $R^{36}$ are joined together to form, including the carbon atoms to which they are attached and the imide nitrogen, an unsubstituted or substituted 5-20-membered monocyclic or polycyclic saturated or unsaturated ring system, wherein the optional substituents are selected from one or more of the group consisting of $(C_{1-6})$-alkyl, fluoro-substituted $(C_{1-6})$-alkyl, halo, $(C_{1-6})$-alkoxy, fluoro-substituted $(C_{1-6})$-alkoxy, and $(C_{6-14})$-aryl; and $R^{37}$ is selected from the group consisting of H, $(C_{1-6})$-alkyl, $(C_{3-8})$-cycloalkyl, and $(C_{6-14})$-aryl, the latter three groups being optionally substituted with one or more of $(C_{1-6})$-alkyl, fluoro-substituted $(C_{1-6})$-alkyl, halo, $(C_{1-6})$-alkoxy, fluoro-substituted $(C_{1-6})$-alkoxy, and $(C_{6-14})$-aryl; and/or one or more of the carbon atoms is optionally replaced with a heteromoiety selected from the group consisting of O, S, N, NH, and N—$(C_{1-6})$-alkyl;

wherein the compound of Formula (IX) is chiral or achiral;

(ii) said compound comprising one or more hydroxy amides is a compound of Formula (Xa) or (Xb)

(Xa)

$$R^{35} \underset{R^{37}}{\overset{OH}{\underset{N}{\bigwedge}}} \overset{O}{\underset{}{\bigwedge}} R^{36},$$

(Xb)

$$R^{35} \overset{O}{\underset{}{\bigwedge}} \underset{R^{37}}{\overset{OH}{\underset{N}{\bigwedge}}} R^{36}$$

wherein $R^{35}$-$R^{37}$ are as defined for Formula (IX) and (iii) said transition metal hydride is a neutral or cationic complex comprising transition metal Ru, Fe, Rh, Ir, Pd, Cu, or Pt, and coordinated thereto:

(a) one to four ligands selected from the group consisting of:
    a bidentate diphosphine (P—P) ligand, and
    a bidentate diamino (N—N) ligand;
(b) one to three hydride ligands;
(c) zero to two neutral monodentate ligands; and
(d) zero to two anionic monodentate ligands;
wherein if the complex is cationic, the complex further comprises one or more suitable counteranions.

2. The process according to claim 1, wherein the bidentate diphosphine ligand (P—P) is a compound of the Formula (I):

$$R^1R^2P\text{-}Q^1\text{-}PR^3R^4 \qquad (I)$$

wherein
$R^1$, $R^2$, $R^3$, and $R^4$ are independently selected from the group consisting of $(C_{1-20})$-alkyl, $(C_{3-20})$-cycloalkyl, and $(C_{6-18})$-aryl, each group being optionally substituted with one or more substituents independently selected from the group consisting of $(C_{1-6})$-alkyl, fluoro-substituted (C$_{1-6}$)-alkyl, halo, (C$_{1-6}$)-alkoxy, fluoro-substituted (C$_{1-6}$)-alkoxy, and (C$_{6-14}$)-aryl, or R$^1$ and R$^2$ and/or R$^3$ and R$^4$ are joined to form, together with the phosphorus atom to which they are attached, a saturated or unsaturated, monocyclic or polycyclic, and substituted or unsubstituted ring system containing from 3 to 14 atoms; and Q$^1$ is selected from the group consisting of unsubstituted or substituted (C$_{1-10}$)-alkylene and unsubstituted or substituted (C$_{2-10}$-alkenylene, wherein, if substituted:
  i) one or more of the available hydrogen atoms on the group are replaced with a substituent independently selected from the group consisting of (C$_{1-6}$)-alkyl, fluoro-substituted (C$_{1-6}$)-alkyl, halo, (C$_{1-6}$)-alkoxy, fluoro-substituted (C$_{1-6}$)-alkoxy and unsubstituted or substituted (C$_{6-14}$)-aryl; and/or
  ii) adjacent available hydrogen atoms on Q$^1$ are replaced with substituents joined together to form, including the carbon atoms to which they are attached, one or more unsubstituted or substituted 5-20-membered monocyclic or polycyclic, heterocyclic, carbocyclic, or metallocenyl, and saturated or unsaturated ring systems;
wherein Q$^1$ is chiral or achiral.

3. The process according to claim 2, wherein R$^1$, R$^2$, R$^3$ and R$^4$ are independently selected from the group consisting of (C$_{1-6}$)-alkyl, (C$_{3-10}$)-cycloalkyl and phenyl, each group being optionally substituted with one to three substituents independently selected from the group consisting of (C$_{1-4}$)-alkyl, fluoro-substituted (C$_{1-4}$)-alkyl, halo, (C$_{1-4}$)-alkoxy and fluoro-substituted (C$_{1-4}$)-alkoxy; and Q$^1$ is selected from the group consisting of unsubstituted or substituted (C$_{1-8}$)-alkylene, wherein, if substituted:
  (i) one to three of the available hydrogen atoms on the group are replaced with a substituent independently selected from the group consisting of (C$_{1-4}$)-alkyl, fluoro-substituted (C$_{1-4}$)-alkyl, halo, (C$_{1-4}$)-alkoxy, fluoro-substituted (C$_{1-4}$)-alkoxy, unsubstituted and substituted phenyl and substituted and unsubstituted naphthyl; and/or (ii) adjacent available hydrogen atoms on Q$^1$ are replaced with substituents joined together to form, including the carbon atoms to which they are attached, one or more unsubstituted or substituted phenylene, cyclohexylene, naphthylene, pyridylene or ferrocenylene groups;
wherein Q$^1$ is chiral or achiral.

4. The process according to claim 3, wherein R$^1$, R$^2$, R$^3$ and R$^4$ are all cyclohexyl, phenyl, xylyl or tolyl.

5. The process according to claim 2, wherein the compound of the Formula (I) is

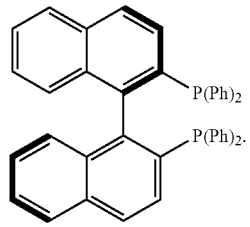

6. The process according to claim 1, wherein the bidentate diamino (N—N) ligand is a compound of the Formula (II):

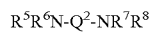

wherein
R$^5$, R$^6$, R$^7$ and R$^8$ are independently selected from the group consisting of H, (C$_{1-20}$)-alkyl, (C$_{3-10}$)-cycloalkyl, and (C$_{6-18}$)-aryl, the latter three groups each being optionally substituted with one or more substituents independently selected from the group consisting of (C$_{1-6}$)-alkyl, fluoro-substituted (C$_{1-6}$)-alkyl, halo, (C$_{1-6}$)-alkoxy, fluoro-substituted (C$_{1-6}$)-alkoxy and (C$_{6-14}$)-aryl, or
R$^5$ and R$^6$ and/or R$^7$ and R$^8$ are joined to form, together with the nitrogen atom to which they are attached, a saturated or unsaturated, monocyclic or polycyclic, and substituted or unsubstituted ring system containing from 3 to 14 atoms; or one of R$^5$ and R$^6$ and/or one of R$^7$ and R$^8$ are joined with a substituent on Q$^2$ to form, together with the nitrogen atom to which R$^5$, R$^6$, R$^7$ or R$^8$ is attached, a 4- to 10-membered saturated or unsaturated and monocyclic or bicyclic ring system, where if the nitrogen atom is part of an aromatic ring or is bonded to an adjacent atom via a double bond, the other of R$^5$ or R$^6$ and R$^7$ or R$^8$ is not present; and
Q$^2$ is selected from the group consisting of unsubstituted or substituted (C$_1$-C$_{10}$)-alkylene and unsubstituted or substituted (C$_2$-C$_{10}$)-alkenylene wherein, if substituted:
  (i) one or more of the available hydrogen atoms on the group are replaced with a substituent independently selected from the group consisting of (C$_{1-6}$)-alkyl, fluoro-substituted (C$_{1-6}$)-alkyl, halo, (C$_{1-6}$)-alkoxy, fluoro-substituted (C$_{1-6}$)-alkoxy and unsubstituted or substituted (C$_{6-14}$)-aryl; and/or (ii) adjacent available hydrogen atoms on Q$^2$ are replaced with substituents joined together to form, including the carbon atoms to which they are attached, one or more unsubstituted or substituted 5-20-membered monocyclic or polycyclic, heterocyclic, carbocyclic, or metallocenyl, and saturated or unsaturated ring systems;
wherein Q$^2$ is chiral or achiral.

7. The process according to claim 6, wherein R$^5$, R$^6$, R$^7$ and R$^8$ are independently selected from the group consisting of H, (C$_{1-6}$)-alkyl, (C$_{3-10}$)-cycloalkyl and phenyl, the latter three groups each being optionally substituted with one to three substituents independently selected from the group consisting of (C$_{1-4}$)-alkyl, fluoro-substituted (C$_{1-4}$)-alkyl, halo, (C$_{1-4}$)-alkoxy and fluoro-substituted (C$_{1-4}$)-alkoxy; and Q$^2$ is selected from the group consisting of unsubstituted or substituted (C$_1$-C$_8$)-alkylene, wherein, if substituted:
  (i) one to three of the available hydrogen atoms on the group are replaced with a substituent independently selected from the group consisting of (C$_{1-4}$)-alkyl, fluoro-substituted (C$_{1-4}$)-alkyl, halo, (C$_{1-4}$)-alkoxy, fluoro-substituted (C$_{1-4}$)-alkoxy, unsubstituted and substituted phenyl and substituted and unsubstituted naphthyl; and/or (ii) adjacent available hydrogen atoms on Q$^2$ are replaced with substituents joined together to form, including the carbon atoms to which they are attached, one or more unsubstituted or substituted phenylene, cyclohexylene, naphthylene, pyridylene or ferrocenylene groups;
wherein Q$^2$ is chiral or achiral.

8. The process according to claim 7, wherein R$^5$, R$^6$, R$^7$ and R$^8$ are all H or (C$_{1-6}$)-alkyl.

9. The process according to claim 8, wherein the optional substituents on Q$^2$ are selected from the group consisting of (C$_{1-4}$)-alkyl, and, substituted or unsubstituted phenyl.

10. The process according to claim 9, wherein the optional substituents on Q$^2$ are selected from the group consisting of iso-propyl, phenyl, and 4-methoxyphenyl.

11. The process according to claim 6, wherein the compound of the Formula (II) is

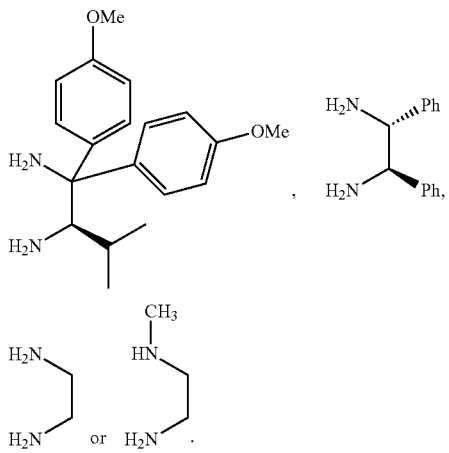

12. The process according to claim 1, wherein the transition metal hydride catalyst is selected from the group consisting of:

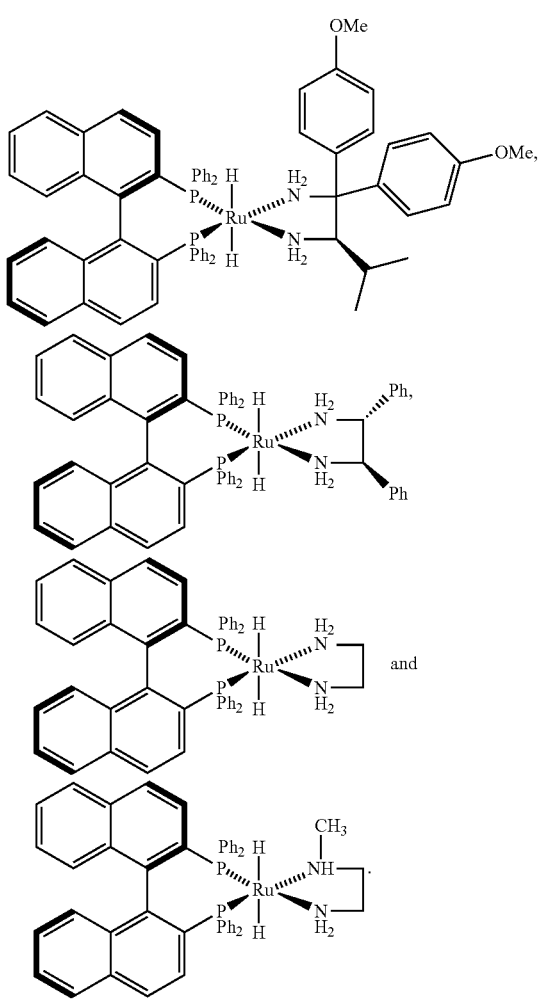

13. The process according to claim 1, wherein $R^{37}$ is H, $(C_{1-3})$-alkyl, $(C_{3-6})$-cycloalkyl, or phenyl, the latter three groups each being optionally substituted, wherein the optional substituents are independently selected from the group consisting of $(C_{1-6})$-alkyl, fluoro-substituted $(C_{1-6})$-alkyl, halo, $(C_{1-6})$-alkoxy, fluoro-substituted $(C_{1-6})$-alkoxy, and phenyl.

14. The process according to claim 1, wherein $R^{35}$ and $R^{36}$ are joined together to form, including the carbon atoms to which they are attached and the imide nitrogen, a polycyclic $(C_{8-12})$-cycloalkyl or $(C_{8-12})$-cycloalkenyl ring system, each being optionally substituted with one to five substituents independently selected from the group consisting of $(C_{1-6})$-alkyl, fluoro-substituted $(C_{1-6})$-alkyl, halo, $(C_{1-6})$-alkoxy, fluoro-substituted $(C_{1-6})$-alkoxy, and $(C_6)$-aryl; and in which one to five carbon atoms in the polycyclic $(C_{8-12})$-cycloalkyl or $(C_{8-12})$-cycloalkenyl ring system are optionally replaced with a heteromoiety selected from the group consisting of O, N, NH, N—$(C_{1-6})$-alkyl, and S.

15. The process according to claim 1, wherein $R^{35}$ and $R^{36}$ are joined to form, including the carbon atoms to which they are attached and the imide nitrogen, a ring system selected from the group consisting of:

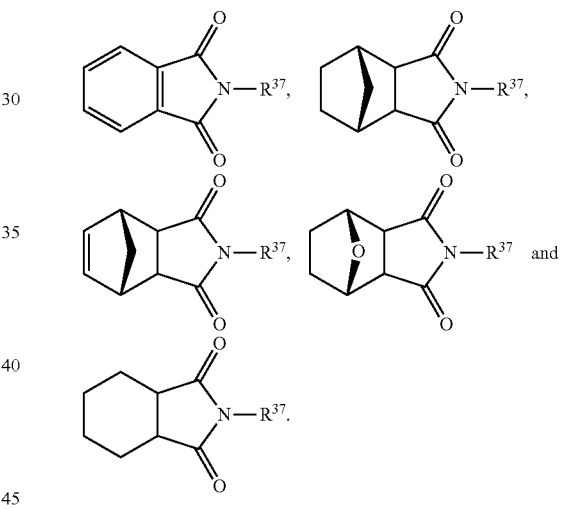

16. The process according to claim 1, wherein said complex comprises one or two neutral monodentate ligands selected from water, acetonitrile, DMF, ammonia, pyridine, tetrahydrofuran (THF), CO, tBuCN, and t-BuNC.

17. The process according to claim 1, wherein said complex comprises one or two anionic monodentate ligands selected from halo, $(C_1$-6)-alkoxy, hydroxy, thiocyanate, cyano, carboxylate, sulfonates, and nitrates anions.

18. The process according to claim 1, wherein the counteranion is $OTf^-$, $BF_4^-$, or $PF_6^-$.

19. The process according to claim 1, wherein the base is an organic non-coordinating base, a carbonate salt, a carboxylate salt, an alcoholate salt, a hydroxide salt, or a silazide salt.

20. The process according to claim 1, wherein the process is performed in a solvent selected from the group consisting of tetrahydrofuran, diethyl ether, chlorinated solvents, toluene, and mixtures thereof.

21. The process according to claim 1, wherein the hydrogen gas is used at a pressure in the range of about 1 atm to about 100 atm.

22. The process according to claim 1, wherein the process is performed at a temperature of about −20° C. to about 60° C.

* * * * *